(12) United States Patent
Brodeur et al.

(10) Patent No.: US 7,553,659 B2
(45) Date of Patent: Jun. 30, 2009

(54) CHD5 ENCODING NUCLEIC ACIDS, POLYPEPTIDES, ANTIBODIES AND METHODS OF USE THEREOF

(75) Inventors: Garrett M. Brodeur, Wynnewood, PA (US); Peter S. White, Drexel Hill, PA (US)

(73) Assignee: The Children's Hospital Of Philadelphia, Philadelphia, PA (US)

( * ) Notice: Subject to any disclaimer, the term of this patent is extended or adjusted under 35 U.S.C. 154(b) by 1042 days.

(21) Appl. No.: 10/462,261

(22) Filed: Jun. 16, 2003

(65) Prior Publication Data

US 2004/0029248 A1    Feb. 12, 2004

Related U.S. Application Data

(60) Provisional application No. 60/388,848, filed on Jun. 14, 2002.

(51) Int. Cl.
  C12N 5/00    (2006.01)
  C12N 1/20    (2006.01)
  C07H 21/02   (2006.01)

(52) U.S. Cl. .................. 435/325; 435/320.1; 435/69.1; 435/252.3; 435/254.11; 536/23.1; 536/23.2; 536/24.3

(58) Field of Classification Search .............. 536/23.1, 536/23.2; 530/350
See application file for complete search history.

(56) References Cited

OTHER PUBLICATIONS

Ngo et al. in The Protein Folding Problem and Tertiary Structure Prediction, 1994, Merz et al. (ed.), Birkhauser, Boston, MA, pp. 433 and 492-495.*

Thompson et al., GenEMBL database Accession No. AF425231.1, Mar. 28, 2002.*

Ahringer, NuRD and SIN3 histone deacetylase complexes in development, TIG (2000) V. 16(8), pp. 351-355.

Ayer et al., Mad-Max Transcriptional Repression is Mediated by Ternary Complex Formation with Mammalian Homologs of Yeast Repressor SIN3, Cell (1995) V. 80, pp. 767-776.

Bentley et al., The physical maps for sequencing human chromosomes 1, 6, 9, 10, 13, 20, and X, Nature (2001), V. 409, pp. 942-943.

Brehm et al., Retinoblastoma protein recruits histone deacetylase to repress transcription, Nature (1998) V. 391(5), pp. 597-601.

Brehm et al., The E7 oncoprotein associates with Mi2 and histone deacetylase activity to promote cell growth, The EMBO Journal (1999) V. 18(9), pp. 2449-2458.

Brodeur et al., Biology and Genetics of Human Neuroblastomas, Journal of Pediatric Hematology/Oncology (1997), V. 19(2), pp. 93-101.

Caron et al., Evidence for two tumour suppressor loci on chromosomal bands 1p35-36 involved in neuroblastoma: one probably imprinted, another associated with N-myc amplification, Human Molecular Genetics (1995) V. 4(4), pp. 535-539.

Cohn et al., Prolonged N-*myc* protein half-life in a neuroblastoma cell line lacking N-*myc* amplification, Oncogene (1990) V. 5, pp. 1821-1827.

Delmas et al., A mammalian DNA-binding protein that contains a chromodomain and an SNF2/SW12-like helicase domain, PNAS (1993), V. 90, pp. 2414-2418.

Eggert et al., Direct Effects of TrkA Expression in Neuroblastoma Cell Lines With or Without *MYCN* Amplification, Medical and Pediatric Oncology (2000), V. 35, pp. 623-627.

Eggert et al., Molecular dissection of TrkA signal transduction pathways mediating differentiation in human neuroblastoma cells, Oncogene (2000), V. 19, pp. 2043-2051.

Ge et al., Molecular Analysis of a Major Antigenic Region of the 240-kD Protein of Mi-2 Autoantigen, J. Clin. Invest. (1995), V. 96, pp. 1730-1737.

Grant et al., Yeast Gcn5 functions in two multisubunit complexes to acetylate nucleosomal histones: characterization of an Ada complex and the SAGA (Spt/Ada) complex, Genes and Development (1997), V. 11, pp. 1640-1650.

Grignani et al., Fusion proteins of the retinoic acid receptor-α recruit histone deacetylase in promyelocytic leukaemia, Nature (1998) V. 391, pp. 815-818.

Harper et al., Sin3 corepressor function in Myc-induced transcription and transformation, PNAS (1996), V. 93, pp. 8536-8540.

Hogarty et al., Identification of a 1-Megabase Consensus Region of Deletion at 1p36.3 in Pirmary Neuroblastomas, Medical and Pediatric Oncology (2000), 35, pp. 512-515.

Kasten et al., SIN3-Dependent Transcriptional Repression by Interaction with the Mad1 DNA-Binding Protein, Molecular and Cellular Biology (1996), V. 16(8), pp. 4215-4221.

Kehle et al., dMi-2, a Hunchback-Interacting Protein that Functions in *Polycomb* Repression, Science (1998), V. 282, pp. 1897-1900.

Kitamura et al., Histone deacetylase inhibitor but not arsenic trioxide differentiates acute promyelocytic leukaemia cells with t(11;17) in combination with all-*trans* retinoic acid, British Journal of Haematology (2000), V. 108, pp. 696-702.

Kozak, Do the 5' untranslated domains of Human cDNAs Challenge the Rules for Initiation of Translation (or Is It Vice Versa)?, Genomics (2000), V. 70, pp. 396-406.

Lin et al., Role of histone deacetylase complex in acute promyelocytic leukaemia, Nature (1998), V. 391 pp. 811-814.

Lipshutz et al., High density synthetic oligonucleotide arrays, nature genetics supplement, (1999), V. 21 pp. 20-24.

Luo et al., Rb interacts with Histone Deacetylase to Repress Transcription, (1998), V. 92, pp. 463-473.

(Continued)

*Primary Examiner*—Richard G Hutson
(74) *Attorney, Agent, or Firm*—Dann, Dorfman, Herrell & Skillman; Robert C. Netter; Kathleen D. Rigaut

(57) ABSTRACT

Nucleic acid sequences encoding chromodomain helicase DNA-binding (CHD) proteins, CHD proteins, and antibodies thereto and methods of use thereof are disclosed.

14 Claims, 4 Drawing Sheets

OTHER PUBLICATIONS

Magnaghi-Jaulin et al., Retinoblastoma protein represses transcription by recruiting a histone deacetylase, Nature (1998), V. 391, pp. 601-605.

Maris et al., Cloning, Chromosomal Localization, Physical Mapping, and Genomic Characterization of HKR3, Genomics (1996), V. 35, pp. 289-298.

Maris et al., Comprehensive Analysis of Chromosome 1p Deletions in Neuroblastoma, Medical and Pediatric Oncology (2001), V. 36, pp. 32-36.

Müller et al., Transcriptional silencing by the Polycomb protein in *Drosphilia* embryos, The EMBO Journal (1995), pp. 1209-1220.

Owen-Hughes et al., Analysis of Nucleosome Disruption by ATP-Driven Chromatin Remodeling Complexes, Methods in Molecular Biology V. 119, pp. 319-331.

Owen-Hughes et al., Remodeling the chromatin structure of a nucleosome array by transcription factor-targeted *trans*-displacement of histones, The EMBO Journal (1996), V. 15(17), pp. 4702-4712.

Reese et al., Genome Annotation Assessment in *Drosophilia melanogaster*, Genome Research (2000), V. 10, pp. 483-501.

Reynolds et al., Biological Classification of Cell Lines Derived from Human Extra-cranial Neural Tumors, Advances in Neuroblastoma Research 2, (1988), pp. 291-306.

Rundlett et al., HDA1 and RPD3 are members of distinct yeast histone deacetylase complexes that regulate silencing and transcription, PNAS, (1996) V. 93, pp. 14503-14508.

Schmidt et al., Molecular Association between ATR and Two Components of the Nucleosome Remodeling and Deacetylating Complex, HDAC2 and CHD4+, Biochemistry, (1999), V. 38, pp. 14711-14717.

Schreiber-Agus et al., An Amino-Terminal Domain of Mxi1 Mediates Anti-Myc Oncogenic Activity and Interacts with a Homolog of the Yeast Transcription Repressor SIN3, Cell (1995), V. 80, pp. 777-786.

Schreiber-Agus et al., Repression by the Mad(Mxi1)-Sin3 complex, BioEssays, (1998), V. 20, pp. 808-818.

Schuster et al., CHD5 defines a new subfamily of chromodomain-SW12/SNF2-like helicases, Mammalian Genome, (2002), V. 13, pp. 117-119.

Seelig et al., The Major Dematomyositis-specific Mi-2 Autoantigen is a Presumed Helicase Involved in Transcriptional Activation, Arthritis and Rheumatism, (1995), V. 38 N. 10, pp. 1389-1399.

Slavotinek et al., Monosomy 1p36, J. Med. Genet., (1999), V. 36, pp. 657-663.

Struhl, Histone acetylation and transcriptional regulatory mechanisms, Genes and Development, (1998), V. 12, pp. 599-606.

Surapureddi et al., Identification of a transcriptionally active peroxisome proliferator-activated receptor α-interacting cofactor complex in rat liver and characterization of PRIC285 as a cofactor, PNAS (2002), V. 99, N. 18, pp. 11836-11841.

Sudarsanam et al., The Swi/Snf family nucleosome-remodeling complexes and transcriptional control, TIG (2000), V. 16, N. 8, pp. 345-350.

Tatusova et al., BLAST 2 Sequences, a new tool for comparing protein and nucleotide sequences, FEMS Microbiology Letters 174 (1999), pp. 247-250.

Thompson et al., Homozygous Deletion of CDKN2A (p16$^{INK4a}$/p14$^{ARF}$) but not within 1p36 or at Other Tumor Supressor Loci in Neuroblastoma, Cancer Research (2001), V. 61, pp. 679-686.

Thompson et al., CHD5, a new member of the chromodomain gene family, is preferentially expressed in the nervous system, Oncogene, (2003), V. 22, N. 7, pp. 1002-1011.

Tong et al., Chromatin deacetylation by an ATP-dependent nucleosome remodeling complex, Nature (1998), V. 395, pp. 917-921.

Wang et al., Architectural DNA binding by a high-mobility-group/kinesin-like subunit in mammalian SWI/SNF-related complexes, PNAS (1998), V. 95 pp. 492-498.

White et al., Molecular Analysis of the Region of Distal 1p Commonly Deleted in Neuroblastoma, European Journal of Cancer (1997), V. 33, N. 12, pp. 1957-1961.

White et al, Detailed Molecular Analysis of 1p36 in Neuroblastoma, Medical and Pediatric Oncology, (2001), V. 36, pp. 36-41.

Wong et al., BRG1, a Component of the SWI-SNF Complex, Is Mutated in Multiple Human Tumor Cell Lines, Cancer Research (2000), V. 60, pp. 6171-6177.

Woodage et al., Characterization of the CHD family of proteins, PNAS (1997), V. 94, pp. 11472-11477.

Wu et al., Molecular refinement of the 1p36 deletion syndrome reveals size diversity and a preponderance of maternally derived deletions., Human Molecular Genetics, (1999), V. 8, N. 2, pp. 313-321.

Xue et al., NURD, a Novel Complex with Both ATP-Dependent Chromatin Remodeling and Histone Deacetylase Activities, Molecular Cell, (1998), V. 2, pp. 851-861.

Yarden et al., BRCA1 interacts with components of the histone deacetylase complex, PNAS, (1999), V. 96, pp. 4983-4988.

Zhang et al., The Dematomyositis-Specific Autoantigen Mi2 Is a Component of a Complex Containing Histone Deacetylase and Nucleosome Remodeling Activities, Cell (1998), V. 95, pp. 279-289.

SPTREMBL Data Base Acc#Q9UFR9 Poustka A. Hypothetical protein KIAA044 May 1, 2000. Alignment with SID No. 2.

PIR Data Base Acc#T17269 Poustka A. Hypothetical protein DKFZp434N23.1 Oct. 15, 1999. Alignment with SID No. 2.

Geneseq Data Base Acc#AAE36108 Friedman L. Human chromodomain helicase DNA binding protein Dec. 12, 2002 (priority date Jun. 4, 2001). Alignment with SID No. 2.

\* cited by examiner

SEQUENCE LISTING

<160> NUMBER OF SEQ ID NOS: 69

<210> SEQ ID NO 1
<211> LENGTH: 9646
<212> TYPE: DNA
<213> ORGANISM: Homo Sapiens

<400> SEQUENCE: 1

```
tcgcccgccg cgcgcgccgg tccggcagcg cacgggttaa ggctggcacc gcgcccggcg      60
ggaggggggg cgcccacctc ccctcctccc cgcgccgggc atgcggggcc cagtgggcac     120
cgaggaggag ctgccgcggc tgttcgccga ggagatggag aatgaggacg agatgtcaga     180
agaagaagat ggtggtcttg aagccttcga tgactttttc cctgtggagc ccgtgagcct     240
tcctaagaag aagaaaccca agaagctcaa ggaaaacaag tgtaaaggga agcggaagaa     300
gaaagagggg agcaatgatg agctatcaga gaatgaagag gatctggaag agaagtcgga     360
gagtgaaggc agtgactact ccccgaataa aaagaagaag aagaaactca aggacaagaa     420
ggagaaaaaa gccaagcgaa aaaagaagga tgaggatgag gatgataatg atgatggatg     480
cttaaaggag cccaagtcct cggggcagct catggccgag tggggcctgg acgacgtgga     540
ctacctgttc tcggaggagg attaccacac gctgaccaac tacaaggcct tcagccagtt     600
cctcaggcca ctcattgcca agaagaaccc gaagatcccc atgtccaaaa tgatgaccgt     660
cctgggtgcc aagtggcggg agttcagcgc caacaacccc ttcaagggca gctccgcggc     720
agcagcggcg gcggcggtgg ctgcggctgt agagacggtc accatctccc ctccgctagc     780
cgtcagcccc cgcaggtgc cccagcctgt gcctatccgc aaggccaaga ccaaggaggg     840
```

```
caaagggcct ggagtgagga agaagatcaa aggctccaaa gatgggaaga aaaagggcaa    900
agggaaaaag acggccgggc tcaagttccg cttcgggggg atcagcaaca agaggaagaa    960
aggctcctcg agtgaagaag atgagaggga ggagtcggac ttcgacagcg ccagcatcca   1020
cagtgcctcc gtgcgctccg aatgctctgc agccctgggc aagaagagca gaggaggcg   1080
caagaagaag aggattgatg atggtgacgg ctatgagaca gaccaccagg attactgtga   1140
ggtgtgccag cagggtgggg agatcatcct gtgcgacacc tgcccgaggg cctaccatct   1200
cgtatgcctg gacccagagc tggagaaggc tcccgagggc aagtggagct gcccccactg   1260
tgagaaggag gggatccagt gggagccgaa ggacgacgac gatgaagagg aggagggcgg   1320
ctgcgaggag gaggaggacg accacatgga gttctgccgc gtgtgcaagg acggggggcga   1380
gctgctctgc tgcgacgcct gcccctcctc ctaccacctg cattgcctca acccgccgct   1440
gcccgagatc ccaaacggtg aatggctctg cccgcgctgt acttgccccc cactgaaggg   1500
caaagtccag cggattctac actggaggtg gacgagccc cctgcccct tcatggtggg   1560
gctgccgggg cctgacgtgg agcccagcct ccctccacct aagcccctgg agggcatccc   1620
tgagagagag ttctttgtca gtgggcagg gctgtcctac tggcattgct cctgggtgaa   1680
ggagctacag ctggagctgt accacacggt gatgtatcgc aactaccaaa gaaagaacga   1740
catggatgag ccgccccct ttgactacgg ctctggggat gaagacggca agagcgagaa   1800
gaggaagaac aaggaccccc tctatgccaa gatggaggag cgcttctacc gctatggcat   1860
caagccagag tggatgatga ttcaccgaat cctgaaccat agctttgaca agaaggggga   1920
tgtgcactac ctgatcaagt ggaaagacct gccctacgac cagtgcacct gggagatcga   1980
tgacatcgac atcccctact acgacaacct caagcaggcc tactggggcc acagggagct   2040
gatgctggga gaagacacca ggctgcccaa gaggctgctc aagaagggca gaagctgag   2100
ggacgacaag caggagaagc cgccggacac gcccattgtg accccacgg tcaagttcga   2160
caagcagcca tggtacatcg actccacagg cggcacactg caccctacc agctggaggg   2220
cctcaactgg ctgcgcttct cttgggccca gggcactgac accatcctgg ccgatgagat   2280
gggtctgggc aagacggtgc agaccatcgt gttcctttac tccctctaca aggagggcca   2340
ctccaaaggg ccctacctgg ttagcgcgcc cctctccacc atcatcaact gggaacgcga   2400
gtttgagatg tgggcgcccg acttctacgt ggtcacctac acggggggaca aggagagccg   2460
ctcggtgatt cggagaacg agttttcctt tgaggacaac gccattcgga gtgggaagaa   2520
ggtattccgt atgaagaaag aagtgcagat caaattccac gtgctgctca cctcctatga   2580
gctcatcacc attgaccagg ccatcctggg ctccatcgag tgggcctgcc tggtggtaga   2640
tgaggcccac cgcctcaaga caaccagtc caagtttttt agggtcttaa acagctacaa   2700
gattgattac aagctgctgc tgacagggac ccccttcag aacaacctgg aggagctgtt   2760
ccatctcctc aacttcctga ctccagagag gttcaacaac ctggagggct tcctggagga   2820
gtttgctgac atctccaagg aagaccagat caagaagctg catgacctgc tggggccgca   2880
catgctcagg cggctcaagg ctgacgtgtt caagaacatg ccggccaaga ccgagctcat   2940
tgtccgggtg gagctgagcc agatgcagaa gaagtactac aagttcatcc tcacacggaa   3000
ctttgaggca ctgaactcca gggggggcgg gaaccaagta tcgctgctca acatcatgat   3060
ggacctgaaa aagtgctgca accaccccta cctcttccct gtggctgccg tggaggcccc   3120
tgtcttgccc aatggctcct acgatggaag ctccctggtc aagtcttcag ggaagctcat   3180
gctgctacag aagatgctga agaaactgcg ggatgagggg caccgtgtgc tcatcttctc   3240
```

```
ccagatgacc aagatgctgg acctcctgga ggacttcctg gagtacgaag gctacaagta    3300
tgagcggatt gatggtggca tcaccggggg cctccggcag gaggcaatcg acagattcaa    3360
tgcccccggg gcccagcagt tctgcttcct cctctcaacc cgggcaggtg gtctgggcat    3420
caacctggcc acggcggaca ctgtcatcat ctacgactcg gactggaacc cgcacaatga    3480
catccaggcc ttcagccgcg cccaccgcat cggccagaac aagaaggtga tgatctaccg    3540
cttcgtgact cgggcctcgg tggaggagcg catcacgcag gtggccaagc gcaagatgat    3600
gctcacccac ctggtggtgc ggcccggcct cggctccaag tcggggtcca tgaccaagca    3660
ggagctggac gacatcctca agttcggcac ggaggaactc ttcaaggacg acgtggaggg    3720
catgatgtct cagggccaga ggccggtcac acccatccct gatgtccagt cctccaaagg    3780
ggggaacttg gccgccagtg caaagaagaa gcacggtagc accccgccag gtgacaacaa    3840
ggacgtggag gacagcagtg tgatccacta tgacgatgcg gccatctcca agctgctgga    3900
ccggaaccag gacgctacag atgacacgga gctacagaac atgaacgagt acctgagctc    3960
cttcaaggtg gcgcagtacg tggtgcgcga ggaggacggc gtggaggagg tggagcggga    4020
aatcatcaag caggaggaga acgtggaccc cgactactgg gagaagctgc tgcggcacca    4080
ctatgagcag cagcaggagg acctggcccg caacctgggc aagggcaagc gcatccgcaa    4140
gcaggtcaac tacaacgatg cctcccagga ggaccaggag tggcaggatg agctctctga    4200
taaccagtca gaatattcca ttggctctga ggatgaggat gaggactttg aagagaggcc    4260
ggaagggcag agtggacgac gacaatcccg gaggcagctg aagagtgaca gggacaagcc    4320
cctgcccccg cttctcgccc gagttggtgg caacatcgag gtgctgggct tcaatgcccg    4380
acagcggaag gcctttctga cgccatcat gcgctgggc atgcccccgc aggacgcctt    4440
caactcccac tggctggtgc gggaccttcg agggaagagc gagaaggagt ttagagccta    4500
tgtgtccctc ttcatgcggc acctgtgtga gccgggggcg gatggtgcag agaccttcgc    4560
agacggcgtg ccccgggagg gcctctccag gcagcacgtg ctgacccgca tcggggtcat    4620
gtcactagtt aggaagaagg ttcaggagtt tgagcatgtc aacgggaagt acagcacccc    4680
agacttgatc cctgaggggc cgaggggaa gaagtcgggc gaggtgatct cctcggaccc    4740
caacacacca gtgcccgcca gccctgccca cctcctgcca gccccgctgg gcctgccaga    4800
caaaatggaa gcccagctgg gctacatgga tgagaaagac cccggggcac agaagccaag    4860
gcagcccctg gaagtccagg cccttccagc cgccttggat agagtggaga gtgaggacaa    4920
gcacgagagc ccagccagca aggagagagc ccgagaggag cggccagagg agacggagaa    4980
ggcccccgcc tccccggagc agctgccgag agaggaggtg cttcctgaga aggagaagat    5040
cctggacaag ctggagctga gcttgatcca cagcagaggg gacagttccg aactcaggcc    5100
agatgacacc aaggctgagg agaaggagcc cattgaaaca cagcaaaatg gtgacaaaga    5160
ggaagatgac gaggggaaga aggaggacaa gaagggaaa ttcaagttca gtgttcaacat    5220 cgcggacggg gcttcacgg agttgcacac gctgtggcag aacgaggagc gggctgctgt    5280
atcctctggg aaaatctacg acatctggca ccggcgccat gactactggc tgctggcggg    5340
catcgtgacg cacggctacg cccgctggca ggacatccag aatgacccac ggtacatgat    5400
cctcaacgag cccttcaagt ctgaggtcca aagggcaac tacctggaga tgaagaacaa    5460
gttcctggcc cgcaggttta gctgctgga gcaggcgttg gtcattgagg agcagctccg    5520
gagggccgcg tacctgaaca tgacgcagga ccccaaccac cccgcccatgg ccctcaacgc    5580
```

-continued

```
ccgcctggct gaagtggagt gcctcgccga gagccaccag cacctgtcca aggagtccct    5640
tgctgggaac aagcctgcca atgccgtcct gcacaaggtc ctgaaccagc tggaggagct    5700
gctgagcgac atgaaggccg acgtgacccg gctgccatcc atgctgtccc gcatcccccc    5760
ggtggccgcc cggctgcaga tgtcggagcg cagcatcctg agccgcctga ccaaccgcgc    5820
cggggacccc accatccagc agggcgcttt cggctcctcc cagatgtaca gcaacaactt    5880
tgggcccaac ttccggggcc ctggaccggg agggattgtc aactacaacc agatgcccct    5940
ggggccctat gtgaccgata tctagccgtc ctcgagactt ccctgtgttg cagcgctcat    6000
ttccagctga gccacgcctg ccgggccacc tgcccgaccc acatgggaga aaaagctgc    6060 cacctttta ggagccagcg ccaccttggg acaaaaggg aaacctagta atgccatcac    6120
atggaggacg aggcccagct cagctgggcc agagcccaga agtgccacct catcataatt    6180
caagtgttct tccacacagc gttgccccca aaccacgcc ggacgtgccc cctcgccacc    6240
ttttccagac gacttcttag aagagatttc atttatttgt acatcttttg cactttccta    6300
ttgaagactt gaacacgttt gtcttgataa aagttggatg acgtatggaa gattcgaacc    6360
tgcagcactg atgtctcttt accgatgggt tccagaccca aggtagtcct ggcactgccc    6420
tgtggactca gcccagctgg ggaggacatg gcgcccggtg ccctaggagc cctcagtgtc    6480
ccctacctga cctgtctgca cctgtgtgac agccccttct gatttggccc cctgcccgct    6540
tggagcctcc cagcaccaga cagggcaggt ttggggagcc gctgtcgagc cctatggtga    6600
gaccctggct gacatttccc ctccttcctg ccaaggctgg aggccgccag gtgtttgctc    6660
tctccttgtg gggaggtgga tcctctgcca gcaggtgtct gtccccggcc cagcgcatct    6720
tgaaggccct ggactctgtt accagtgggg ggctgtggc cccggctctt cacagcaggc    6780
agaagcgtat gatcccaggg agggtgggct ggggggggc cagcacttgc ctcggagcca    6840
ctgctgcgtt gggtttgcct tctgccagag gtgtggttaa gggcagtgat agctgcgccc    6900
cagcaaggag ggtcatgggc cctgagctgg cccaggagac cctggccctg ccctgtgccc    6960
tgggatgcct accctgccca cctccggagg tggaaccggg ctgccctgg ggcctggac    7020 ttgtcccatt cccctgtccc tggaaaggcc ttccggggg ctttttgcct gaggctgcac    7080
tcttggaagg tgtggggaga gttctgcctg gaggggact ggaccagtg ccctctgcag    7140 accctccca gccgcagcac caagggcttg ctgccttgtt tcctgccagg agcgccctga    7200
catcccaaaa ccatcttccc acatgtgggt tgttggaatc ccaccactc ccccggaccc    7260 tgcccctcca agttggggac ggagatgggg agcaggtcag gccctcccta ggcctgtttg    7320
tgtgtgatcc ttctcctggc cccaggtcga cctggaaggc gtttctgagt cttgtactgg    7380
gaccttccca gggaaggtgc cttggggtgc agaatcctgg gaatgttagg aaagggctgc    7440
gtgaaaaacc cagctgggcc tggggtggag gtgcacacgg gctggggctc agctccttgg    7500
agagggcctg cctgggactg aggggccag ggctgggtca ggattcacca gcttgtgttg    7560
cagacactgg agcaattgcc tggccctccc taagccctat atgcctcact cataatgagg    7620
ctgtctctga accccggagg gcgggaccta caagtccttc ctcttggcgc attcccacac    7680
tccagtctgg atccaggtct gcaaggccag cccgaccctg acactgcacg tgggcgtagt    7740
ggggagcacc ctggagtgga gatgattgtc agcgggctca catgttatgg ttcatccaca    7800
tgcgtgttgt gtgctctgcg gtgcctcctg gcaaagggtc ctggctcggg tcagaagctc    7860
actcccgtgc cctcgtcccc aaacaagcag tggcaagcac tggggttggc cctcgttggg    7920
agcagtgccc accttccttg gcccacagca gataggtccc gagcagcagg actggaggcc    7980
```

-continued

```
tgtggcggtc agggcagggg tctgtgtctc caccccaagg gctgatggtc cctcccctgt    8040
gcgccttcct ctcaggcagg cttgctctgt cccttcctct ctgcttccct cccaggcctc    8100
gccagggctc ccttctcctc tgcctggtta gactcgggca cccaggaaag cctggccagg    8160
gctcctttgg gcctgggccc cctgcactgc ctggtccaga aggggtggtg ctgtccgtgg    8220
ccagcacccc ggggcccggg aggggtgggc tactagagtc agagcgggtt tggggctgac    8280
cagtttggga gaggagaaaa gatctgagaa tgtccttctt ggtttgtcag tcatctctgc    8340
caaaagtggt gatggtggtg tccgtatgtt tggcgtcttt gggctgggtt tggttttgc     8400
tgctggtaga atcagggtcc tcgggcatga acgcgagccc aaagtgccag tctgcgattg    8460
gaaatttcca gccactttaa gccagtgctg agtagggctt ctgcagagcc atgtttgagc    8520
caaggtcttg gaaggcattg ccccatgggc tcaggtgact cggggtggag tgagcacgtc    8580
tgcagggccc tctcatacac gcctgaggca gaagcagcgt ccccgtgaa agccaccttc     8640
cgaagctcct gcgttttttg caaacttggc ttcccccagg ggcaggctgg actttccctg    8700
cccctatga ttgaagtcct cctgcttttg ggggctgcct tcccagagtc ccccgggtgc     8760
tcccctgccg aggtcaggag ctgaccaagc cttggcccgg tgacacctgc agccctcact    8820
cctgtcatcc caggacactt gaggcccaag gaggtggagt ggagagtggg ctcgggtaca    8880
tgggagccag aagccagatg gacttggtca agtgttggtc acttggagcc tccagtgtgc    8940
gtcagggtct gtgggcaggg gacagggcgt gggtggggggc cgaggctggc acgcccctct   9000
gccctcaccg tcttggtgac ctggcctcgg cccctccccc aagtctcttc tgtgcaaggc    9060
ccgcctcggc ctcggcagct ggttcctgtc ccgttttctg tgtctgaaag tttacaggtt    9120
gtggtgcatc agcccaaact cactggcgtt gtgtttttt tttctttaat tttcagattt     9180
ttttttaaa caaagtattt ttttaggtgc gataacccag aaagggcccg ttgggtgtgt     9240
gtgtgtgtcc tgaactcctc aagcagcgat tggagcccaa gcacccctgg agaggaaggg    9300
agggtcccca ctggcccgtg gggtctgagt tcagggtgt ggaggagca gactccaccg      9360
gcccaggccc agctaagagg gggccgaccc cttccccag gcacagcccc aggctggcaa     9420
agggagggcc ctgggctggg tgcagggcgc gccaggagtc ccagccaggg tggccccggc    9480
ggggcgggt ccagctttgg aagccaggct ccctgtgag ccgtggcttg tctggtcttc      9540
gcccacggga ggctggacag aggctgtagc caacacaatc acctttactt tgtactctgt    9600
gtgtatgttt tggttttctg tgttttaata aatccttgg gaaagg                    9646
```

<210> SEQ ID NO 2
<211> LENGTH: 1954
<212> TYPE: PRT
<213> ORGANISM: Homo Sapiens

<400> SEQUENCE: 2

Met Arg Gly Pro Val Gly Thr Glu Glu Glu Leu Pro Arg Leu Phe Ala
1               5                   10                  15

Glu Glu Met Glu Asn Glu Asp Glu Met Ser Glu Glu Glu Asp Gly Gly
            20                  25                  30

Leu Glu Ala Phe Asp Asp Phe Phe Pro Val Glu Pro Val Ser Leu Pro
        35                  40                  45

Lys Lys Lys Lys Pro Lys Lys Leu Lys Glu Asn Lys Cys Lys Gly Lys
    50                  55                  60

Arg Lys Lys Lys Glu Gly Ser Asn Asp Glu Leu Ser Glu Asn Glu Glu
65                  70                  75                  80

```
Asp Leu Glu Glu Lys Ser Glu Ser Gly Ser Asp Tyr Ser Pro Asn
                 85                  90                  95

Lys Lys Lys Lys Lys Leu Lys Asp Lys Glu Lys Lys Ala Lys
            100                 105                 110

Arg Lys Lys Asp Glu Asp Asp Asn Asp Asp Gly Cys Leu
        115                 120                 125

Lys Glu Pro Lys Ser Ser Gly Gln Leu Met Ala Glu Trp Gly Leu Asp
        130                 135                 140

Asp Val Asp Tyr Leu Phe Ser Glu Glu Asp Tyr His Thr Leu Thr Asn
145                 150                 155                 160

Tyr Lys Ala Phe Ser Gln Phe Leu Arg Pro Leu Ile Ala Lys Lys Asn
                165                 170                 175

Pro Lys Ile Pro Met Ser Lys Met Met Thr Val Leu Gly Ala Lys Trp
            180                 185                 190

Arg Glu Phe Ser Ala Asn Asn Pro Phe Lys Gly Ser Ser Ala Ala Ala
        195                 200                 205

Ala Ala Ala Ala Val Ala Ala Val Glu Thr Val Thr Ile Ser Pro
    210                 215                 220

Pro Leu Ala Val Ser Pro Pro Gln Val Pro Gln Pro Val Pro Ile Arg
225                 230                 235                 240

Lys Ala Lys Thr Lys Glu Gly Lys Gly Pro Gly Val Arg Lys Lys Ile
                245                 250                 255

Lys Gly Ser Lys Asp Gly Lys Lys Gly Lys Gly Lys Lys Thr Ala
            260                 265                 270

Gly Leu Lys Phe Arg Phe Gly Gly Ile Ser Asn Lys Arg Lys Lys Gly
        275                 280                 285

Ser Ser Ser Glu Glu Asp Glu Arg Glu Glu Ser Asp Phe Asp Ser Ala
    290                 295                 300

Ser Ile His Ser Ala Ser Val Arg Ser Glu Cys Ser Ala Ala Leu Gly
305                 310                 315                 320

Lys Lys Ser Lys Arg Arg Arg Lys Lys Lys Arg Ile Asp Asp Gly Asp
                325                 330                 335

Gly Tyr Glu Thr Asp His Gln Asp Tyr Cys Glu Val Cys Gln Gln Gly
            340                 345                 350

Gly Glu Ile Ile Leu Cys Asp Thr Cys Pro Arg Ala Tyr His Leu Val
        355                 360                 365

Cys Leu Asp Pro Glu Leu Glu Lys Ala Pro Glu Gly Lys Trp Ser Cys
    370                 375                 380

Pro His Cys Glu Lys Glu Gly Ile Gln Trp Glu Pro Lys Asp Asp Asp
385                 390                 395                 400

Asp Glu Glu Glu Glu Gly Gly Cys Glu Glu Glu Asp Asp His Met
                405                 410                 415

Glu Phe Cys Arg Val Cys Lys Asp Gly Gly Glu Leu Leu Cys Cys Asp
        420                 425                 430

Ala Cys Pro Ser Ser Tyr His Leu His Cys Leu Asn Pro Pro Leu Pro
    435                 440                 445

Glu Ile Pro Asn Gly Glu Trp Leu Cys Pro Arg Cys Thr Cys Pro Pro
    450                 455                 460

Leu Lys Gly Lys Val Gln Arg Ile Leu His Trp Arg Trp Thr Glu Pro
465                 470                 475                 480

Pro Ala Pro Phe Met Val Gly Leu Pro Gly Pro Asp Val Glu Pro Ser
                485                 490                 495
```

-continued

```
Leu Pro Pro Pro Lys Pro Leu Glu Gly Ile Pro Glu Arg Glu Phe Phe
            500                 505                 510

Val Lys Trp Ala Gly Leu Ser Tyr Trp His Cys Ser Trp Val Lys Glu
        515                 520                 525

Leu Gln Leu Glu Leu Tyr His Thr Val Met Tyr Arg Asn Tyr Gln Arg
    530                 535                 540

Lys Asn Asp Met Asp Glu Pro Pro Phe Asp Tyr Gly Ser Gly Asp
545                 550                 555                 560

Glu Asp Gly Lys Ser Glu Lys Arg Lys Asn Lys Asp Pro Leu Tyr Ala
                565                 570                 575

Lys Met Glu Glu Arg Phe Tyr Arg Tyr Gly Ile Lys Pro Glu Trp Met
            580                 585                 590

Met Ile His Arg Ile Leu Asn His Ser Phe Asp Lys Lys Gly Asp Val
        595                 600                 605

His Tyr Leu Ile Lys Trp Lys Asp Leu Pro Tyr Asp Gln Cys Thr Trp
    610                 615                 620

Glu Ile Asp Asp Ile Asp Ile Pro Tyr Tyr Asp Asn Leu Lys Gln Ala
625                 630                 635                 640

Tyr Trp Gly His Arg Glu Leu Met Leu Gly Glu Asp Thr Arg Leu Pro
                645                 650                 655

Lys Arg Leu Leu Lys Lys Gly Lys Lys Leu Arg Asp Asp Lys Gln Glu
            660                 665                 670

Lys Pro Pro Asp Thr Pro Ile Val Asp Pro Thr Val Lys Phe Asp Lys
        675                 680                 685

Gln Pro Trp Tyr Ile Asp Ser Thr Gly Gly Thr Leu His Pro Tyr Gln
    690                 695                 700

Leu Glu Gly Leu Asn Trp Leu Arg Phe Ser Trp Ala Gln Gly Thr Asp
705                 710                 715                 720

Thr Ile Leu Ala Asp Glu Met Gly Leu Gly Lys Thr Val Gln Thr Ile
                725                 730                 735

Val Phe Leu Tyr Ser Leu Tyr Lys Glu Gly His Ser Lys Gly Pro Tyr
            740                 745                 750

Leu Val Ser Ala Pro Leu Ser Thr Ile Ile Asn Trp Glu Arg Glu Phe
        755                 760                 765

Glu Met Trp Ala Pro Asp Phe Tyr Val Val Thr Tyr Thr Gly Asp Lys
    770                 775                 780

Glu Ser Arg Ser Val Ile Arg Glu Asn Glu Phe Ser Phe Glu Asp Asn
785                 790                 795                 800

Ala Ile Arg Ser Gly Lys Lys Val Phe Arg Met Lys Lys Glu Val Gln
                805                 810                 815

Ile Lys Phe His Val Leu Leu Thr Ser Tyr Glu Leu Ile Thr Ile Asp
            820                 825                 830

Gln Ala Ile Leu Gly Ser Ile Glu Trp Ala Cys Leu Val Val Asp Glu
        835                 840                 845

Ala His Arg Leu Lys Asn Asn Gln Ser Lys Phe Phe Arg Val Leu Asn
    850                 855                 860

Ser Tyr Lys Ile Asp Tyr Lys Leu Leu Leu Thr Gly Thr Pro Leu Gln
865                 870                 875                 880

Asn Asn Leu Glu Glu Leu Phe His Leu Leu Asn Phe Leu Thr Pro Glu
                885                 890                 895

Arg Phe Asn Asn Leu Glu Gly Phe Leu Glu Glu Phe Ala Asp Ile Ser
            900                 905                 910

Lys Glu Asp Gln Ile Lys Lys Leu His Asp Leu Leu Gly Pro His Met
```

```
                915                 920                 925
Leu Arg Arg Leu Lys Ala Asp Val Phe Lys Asn Met Pro Ala Lys Thr
    930                 935                 940

Glu Leu Ile Val Arg Val Glu Leu Ser Gln Met Gln Lys Lys Tyr Tyr
945                 950                 955                 960

Lys Phe Ile Leu Thr Arg Asn Phe Glu Ala Leu Asn Ser Lys Gly Gly
                965                 970                 975

Gly Asn Gln Val Ser Leu Leu Asn Ile Met Met Asp Leu Lys Lys Cys
            980                 985                 990

Cys Asn His Pro Tyr Leu Phe Pro Val Ala Ala Val Glu Ala Pro Val
        995                 1000                1005

Leu Pro Asn Gly Ser Tyr Asp Gly Ser Ser Leu Val Lys Ser Ser Gly
    1010                1015                1020

Lys Leu Met Leu Leu Gln Lys Met Leu Lys Lys Leu Arg Asp Glu Gly
1025                1030                1035                1040

His Arg Val Leu Ile Phe Ser Gln Met Thr Lys Met Leu Asp Leu Leu
                1045                1050                1055

Glu Asp Phe Leu Glu Tyr Glu Gly Tyr Lys Tyr Glu Arg Ile Asp Gly
            1060                1065                1070

Gly Ile Thr Gly Gly Leu Arg Gln Glu Ala Ile Asp Arg Phe Asn Ala
        1075                1080                1085

Pro Gly Ala Gln Gln Phe Cys Phe Leu Leu Ser Thr Arg Ala Gly Gly
    1090                1095                1100

Leu Gly Ile Asn Leu Ala Thr Ala Asp Thr Val Ile Ile Tyr Asp Ser
1105                1110                1115                1120

Asp Trp Asn Pro His Asn Asp Ile Gln Ala Phe Ser Arg Ala His Arg
                1125                1130                1135

Ile Gly Gln Asn Lys Lys Val Met Ile Tyr Arg Phe Val Thr Arg Ala
            1140                1145                1150

Ser Val Glu Glu Arg Ile Thr Gln Val Ala Lys Arg Lys Met Met Leu
        1155                1160                1165

Thr His Leu Val Val Arg Pro Gly Leu Gly Ser Lys Ser Gly Ser Met
    1170                1175                1180

Thr Lys Gln Glu Leu Asp Asp Ile Leu Lys Phe Gly Thr Glu Glu Leu
1185                1190                1195                1200

Phe Lys Asp Asp Val Glu Gly Met Met Ser Gln Gly Gln Arg Pro Val
                1205                1210                1215

Thr Pro Ile Pro Asp Val Gln Ser Ser Lys Gly Gly Asn Leu Ala Ala
            1220                1225                1230

Ser Ala Lys Lys Lys His Gly Ser Thr Pro Pro Gly Asp Asn Lys Asp
        1235                1240                1245

Val Glu Asp Ser Ser Val Ile His Tyr Asp Asp Ala Ala Ile Ser Lys
    1250                1255                1260

Leu Leu Asp Arg Asn Gln Asp Ala Thr Asp Asp Thr Glu Leu Gln Asn
1265                1270                1275                1280

Met Asn Glu Tyr Leu Ser Ser Phe Lys Val Ala Gln Tyr Val Val Arg
                1285                1290                1295

Glu Glu Asp Gly Val Glu Glu Val Glu Arg Glu Ile Ile Lys Gln Glu
            1300                1305                1310

Glu Asn Val Asp Pro Asp Tyr Trp Glu Lys Leu Leu Arg His His Tyr
        1315                1320                1325

Glu Gln Gln Gln Glu Asp Leu Ala Arg Asn Leu Gly Lys Gly Lys Arg
    1330                1335                1340
```

```
Ile Arg Lys Gln Val Asn Tyr Asn Asp Ala Ser Gln Glu Asp Gln Glu
1345                1350                1355                1360

Trp Gln Asp Glu Leu Ser Asp Asn Gln Ser Glu Tyr Ser Ile Gly Ser
            1365                1370                1375

Glu Asp Glu Asp Glu Asp Phe Glu Glu Arg Pro Glu Gly Gln Ser Gly
        1380                1385                1390

Arg Arg Gln Ser Arg Arg Gln Leu Lys Ser Asp Arg Asp Lys Pro Leu
    1395                1400                1405

Pro Pro Leu Leu Ala Arg Val Gly Gly Asn Ile Glu Val Leu Gly Phe
1410                1415                1420

Asn Ala Arg Gln Arg Lys Ala Phe Leu Asn Ala Ile Met Arg Trp Gly
1425                1430                1435                1440

Met Pro Pro Gln Asp Ala Phe Asn Ser His Trp Leu Val Arg Asp Leu
            1445                1450                1455

Arg Gly Lys Ser Glu Lys Glu Phe Arg Ala Tyr Val Ser Leu Phe Met
        1460                1465                1470

Arg His Leu Cys Glu Pro Gly Ala Asp Gly Ala Glu Thr Phe Ala Asp
    1475                1480                1485

Gly Val Pro Arg Glu Gly Leu Ser Arg Gln His Val Leu Thr Arg Ile
1490                1495                1500

Gly Val Met Ser Leu Val Arg Lys Lys Val Gln Glu Phe Glu His Val
1505                1510                1515                1520

Asn Gly Lys Tyr Ser Thr Pro Asp Leu Ile Pro Glu Gly Pro Glu Gly
            1525                1530                1535

Lys Lys Ser Gly Glu Val Ile Ser Ser Asp Pro Asn Thr Pro Val Pro
        1540                1545                1550

Ala Ser Pro Ala His Leu Leu Pro Ala Pro Leu Gly Leu Pro Asp Lys
    1555                1560                1565

Met Glu Ala Gln Leu Gly Tyr Met Asp Glu Lys Asp Pro Gly Ala Gln
1570                1575                1580

Lys Pro Arg Gln Pro Leu Glu Val Gln Ala Leu Pro Ala Ala Leu Asp
1585                1590                1595                1600

Arg Val Glu Ser Glu Asp Lys His Glu Ser Pro Ala Ser Lys Glu Arg
            1605                1610                1615

Ala Arg Glu Glu Arg Pro Glu Glu Thr Glu Lys Ala Pro Pro Ser Pro
        1620                1625                1630

Glu Gln Leu Pro Arg Glu Glu Val Leu Pro Glu Lys Glu Lys Ile Leu
    1635                1640                1645

Asp Lys Leu Glu Leu Ser Leu Ile His Ser Arg Gly Asp Ser Ser Glu
1650                1655                1660

Leu Arg Pro Asp Asp Thr Lys Ala Glu Glu Lys Glu Pro Ile Glu Thr
1665                1670                1675                1680

Gln Gln Asn Gly Asp Lys Glu Glu Asp Glu Gly Lys Lys Glu Asp
            1685                1690                1695

Lys Lys Gly Lys Phe Lys Phe Met Phe Asn Ile Ala Asp Gly Gly Phe
        1700                1705                1710

Thr Glu Leu His Thr Leu Trp Gln Asn Glu Glu Arg Ala Ala Val Ser
    1715                1720                1725

Ser Gly Lys Ile Tyr Asp Ile Trp His Arg Arg His Asp Tyr Trp Leu
1730                1735                1740

Leu Ala Gly Ile Val Thr His Gly Tyr Ala Arg Trp Gln Asp Ile Gln
1745                1750                1755                1760
```

-continued

```
Asn Asp Pro Arg Tyr Met Ile Leu Asn Glu Pro Phe Lys Ser Glu Val
            1765                1770                1775
His Lys Gly Asn Tyr Leu Glu Met Lys Asn Lys Phe Leu Ala Arg Arg
        1780                1785                1790
Phe Lys Leu Leu Glu Gln Ala Leu Val Ile Glu Gln Leu Arg Arg
        1795                1800                1805
Ala Ala Tyr Leu Asn Met Thr Gln Asp Pro Asn His Pro Ala Met Ala
        1810                1815                1820
Leu Asn Ala Arg Leu Ala Glu Val Glu Cys Leu Ala Glu Ser His Gln
1825                1830                1835                1840
His Leu Ser Lys Glu Ser Leu Ala Gly Asn Lys Pro Ala Asn Ala Val
            1845                1850                1855
Leu His Lys Val Leu Asn Gln Leu Glu Glu Leu Leu Ser Asp Met Lys
            1860                1865                1870
Ala Asp Val Thr Arg Leu Pro Ser Met Leu Ser Arg Ile Pro Pro Val
            1875                1880                1885
Ala Ala Arg Leu Gln Met Ser Glu Arg Ser Ile Leu Ser Arg Leu Thr
        1890                1895                1900
Asn Arg Ala Gly Asp Pro Thr Ile Gln Gln Gly Ala Phe Gly Ser Ser
1905                1910                1915                1920
Gln Met Tyr Ser Asn Asn Phe Gly Pro Asn Phe Arg Gly Pro Gly Pro
            1925                1930                1935
Gly Gly Ile Val Asn Tyr Asn Gln Met Pro Leu Gly Pro Tyr Val Thr
            1940                1945                1950
Asp Ile
```

```
<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
tcatcattgc tccctctttt                                          20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ttcttccgct tccctttaca                                          20

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
ccgagatccc aaacggtg                                            18

<210> SEQ ID NO 6
<211> LENGTH: 21
<212> TYPE: DNA
<213> ORGANISM: Artificial Sequence
```

```
<220> FEATURE:
<223> OTHER INFORMATION: Primer

<400> SEQUENCE: 6
ccagtgtaga atccgctgga c                                              21

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
ctctgcccgc gctgtacttg cc                                             22

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
aggattacca cacgctgacc                                                20

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
gtcttggcct tgcggatag                                                 19

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
aagaagctga gggacgacaa                                                20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gttgatgatg gtggagaggg                                                20

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
tcatctacga ctcggactgg aacc                                           24
```

```
<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
cctttggagg actggacatc ag                                            22

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
aagatgacga ggggaagaag gagg                                          24

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tcaatgacca acgcctgctc                                               20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
aggattacca cacgctgacc                                               20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
ggctcatcca tgtcgttctt                                               20

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
gcagcgcacg ggttaagg                                                 18

<210> SEQ ID NO 19
<211> LENGTH: 18
<212> TYPE: DNA
<213> ORGANISM: Artificial Sequence
<220> FEATURE:
<223> OTHER INFORMATION: Primer
```

<400> SEQUENCE: 19
cgcccacctc ccctcctc                                                        18

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20 cagggggcatc tggttgtagt                                                     20

<210> SEQ ID NO 21
<211> LENGTH: 17
<212> TYPE: DNA
<213> ORGANISM: Artificial Sequence
<220> FEATURE:
<223> OTHER INFORMATION: Primer

<400> SEQUENCE: 21
ccgagatccc aaacggt                                                         17

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
ccagtgtaga atccgctgga c                                                    21

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
ctctgcccgc gctgtacttg cc                                                   22

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
cttcagaaca acctggagga                                                      20

<210> SEQ ID NO 25
<211> LENGTH: 18
<212> TYPE: DNA
<213> ORGANISM: Artificial Sequence
<220> FEATURE:
<223> OTHER INFORMATION: Primer

<400> SEQUENCE: 25
atctcctcgg cgaacagc                                                        18

<210> SEQ ID NO 26

```
<211> LENGTH: 20
<212> TYPE: DNA
<213> ORGANISM: Artificial Sequence
<220> FEATURE:
<223> OTHER INFORMATION: Primer

<400> SEQUENCE: 26
tcatcattgc tccctctctt                                                  20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
ttcttccgct tccctttaca                                                  20

<210> SEQ ID NO 28
<211> LENGTH: 18
<212> TYPE: DNA
<213> ORGANISM: Artificial Sequence
<220> FEATURE:
<223> OTHER INFORMATION: Primer

<400> SEQUENCE: 28
cgcccacctc ccctcctc                                                    18

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
ttctctgata gctcatcatt gc                                               22

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
gtgtaaaggg aagcggaaga                                                  20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
tggctgaagg ccttgtagtt                                                  20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
```

-continued aggattacca cacgctgacc                                               20

<210> SEQ ID NO 33
<211> LENGTH: 19
<212> TYPE: DNA
<213> ORGANISM: Artificial Sequence
<220> FEATURE:
<223> OTHER INFORMATION: Primer

<400> SEQUENCE: 33
gctttggcct tgcggatag                                                19

<210> SEQ ID NO 34
<211> LENGTH: 19
<212> TYPE: DNA
<213> ORGANISM: Artificial Sequence
<220> FEATURE:
<223> OTHER INFORMATION: Primer

<400> SEQUENCE: 34
gcggctgtag agacggtca                                                19

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
gctggcacac ctcacagtaa                                               20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
tggtgacggc tatgagacag                                               20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
gaactccatg tggtcgtcct                                               20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
aggacgacga cgatgaagag                                               20

<210> SEQ ID NO 39
<211> LENGTH: 19
<212> TYPE: DNA

<213> ORGANISM: Artificial Sequence
<220> FEATURE:
<223> OTHER INFORMATION: Primer

<400> SEQUENCE: 39
tccgtccacc tccagtgta                                              19

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
gagatcccaa acggtgaatg                                             20

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
ggctcatcca tgtcgttctt                                             20

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
cacggtgatg tatcgcaact                                             20

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
ttgtcgtccc tcagcttctt                                             20

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
caagaggctg ctcaagaagg                                             20

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
gttgatgatg gtggagaggg                                             20

```
<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
aagaagctga gggacgacaa                                              20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
aggtgaccac gtagaagtcg                                              20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
ccctctccac catcatcaac                                              20

<210> SEQ ID NO 49
<211> LENGTH: 21
<212> TYPE: DNA
<213> ORGANISM: Artificial Sequence
<220> FEATURE:
<223> OTHER INFORMATION: Primer

<400> SEQUENCE: 49
tgaacctctc tggagtcagg a                                            21

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
agaacaacct ggaggagctg                                              20

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
cttccatcgt aggagccatt                                              20

<210> SEQ ID NO 52
<211> LENGTH: 20
<212> TYPE: DNA
<213> ORGANISM: Artificial Sequence
<220> FEATURE:
```

<223> OTHER INFORMATION: Primer

<400> SEQUENCE: 52
acccctacct cttccctgtg                                        20

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
gaaggcctgg atgtcattgt                                        20

<210> SEQ ID NO 54
<211> LENGTH: 24
<212> TYPE: DNA
<213> ORGANISM: Artificial Sequence
<220> FEATURE:
<223> OTHER INFORMATION: Primer

<400> SEQUENCE: 54
tcatctacga ctcggactgg aacc                                   24

<210> SEQ ID NO 55
<211> LENGTH: 22
<212> TYPE: DNA
<213> ORGANISM: Artificial Sequence
<220> FEATURE:
<223> OTHER INFORMATION: Primer

<400> SEQUENCE: 55
cctttggagg actggacatc ag                                     22

<210> SEQ ID NO 56
<211> LENGTH: 19
<212> TYPE: DNA
<213> ORGANISM: Artificial Sequence
<220> FEATURE:
<223> OTHER INFORMATION: Primer

<400> SEQUENCE: 56
gagggcatga tgtctcagg                                         19

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
gcagcttctc ccagtagtcg                                        20

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
gggaaatcat caagcaggag                                        20

```
<210> SEQ ID NO 59
<211> LENGTH: 19
<212> TYPE: DNA
<213> ORGANISM: Artificial Sequence
<220> FEATURE:
<223> OTHER INFORMATION: Primer

<400> SEQUENCE: 59
ctcgatgttg ccaccaact                                                  19

<210> SEQ ID NO 60
<211> LENGTH: 19
<212> TYPE: DNA
<213> ORGANISM: Artificial Sequence
<220> FEATURE:
<223> OTHER INFORMATION: Primer

<400> SEQUENCE: 60
ggaggcgctg aagagtgac                                                  19

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
ctagtgacat gaccccgatg                                                 20

<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
gtgcagagac cttcgcagac                                                 20

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
tcgtgcttgt cctcactctc                                                 20

<210> SEQ ID NO 64
<211> LENGTH: 18
<212> TYPE: DNA
<213> ORGANISM: Artificial Sequence
<220> FEATURE:
<223> OTHER INFORMATION: Primer

<400> SEQUENCE: 64
aaggcagccc ctggaagt                                                   18

<210> SEQ ID NO 65
<211> LENGTH: 19
<212> TYPE: DNA
<213> ORGANISM: Artificial Sequence
<220> FEATURE:
<223> OTHER INFORMATION: Primer
```

```
-continued

<400> SEQUENCE: 65
gtgtgcaact ccgtgaagc                                                19

<210> SEQ ID NO 66
<211> LENGTH: 24
<212> TYPE: DNA
<213> ORGANISM: Artificial Sequence
<220> FEATURE:
<223> OTHER INFORMATION: Primer

<400> SEQUENCE: 66
aagatgacga ggggaagaag gagg                                          24

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
tcaatgacca acgcctgctc                                               20

<210> SEQ ID NO 68
<211> LENGTH: 24
<212> TYPE: DNA
<213> ORGANISM: Artificial Sequence
<220> FEATURE:
<223> OTHER INFORMATION: Primer

<400> SEQUENCE: 68
aagatgacga ggggaagaag gagg                                          24

<210> SEQ ID NO 69
<211> LENGTH: 20
<212> TYPE: DNA
<213> ORGANISM: Artificial Sequence
<220> FEATURE:
<223> OTHER INFORMATION: Primer

<400> SEQUENCE: 69
ggggcaacgc tgtgtggaag                                               20
```

CHD5 ENCODING NUCLEIC ACIDS, POLYPEPTIDES, ANTIBODIES AND METHODS OF USE THEREOF

CROSS REFERENCE TO RELATED APPLICATIONS

This application claims priority under 35 U.S.C. §119(e) to U.S. Provisional Patent Application No. 60/388,848 filed on Jun. 14, 2002, the entire disclosure of which is incorporated by reference herein.

GOVERNMENT RIGHTS

Pursuant to 35 U.S.C. §202(c) it is acknowledged that the U.S. Government has certain rights in the invention described herein, which was made in part with funds from the National Institutes of Health, Grant Number, CA-39771.

FIELD OF INVENTION

This invention relates to the fields of medicine, molecular biology, and Chromodomain, Helicase, DNA-binding (CHD) proteins. Specifically, nucleic and amino acid sequences for expressing the human CHD5 and fragments thereof as well as CHD5 immunospecific antibodies are provided. Methods and kits employing the compositions of the invention are also disclosed.

BACKGROUND OF THE INVENTION

Several publications and patent documents are cited in this application in order to more fully describe the state of the art to which this invention pertains. The disclosure of each of these citations is incorporated by reference herein.

There is strong evidence that gene expression can be affected by changes in chromatin structure and the association of DNA with nucleosomes. The acetylation of lysine residues on histone tails by histone acetyltransferases (HATs) neutralizes their charge and decreases the affinity of histones for DNA. Conversely, the deacetylation of these residues by histone deacetylases (HDACs) restores this affinity and can decrease the accessibility of DNA to transcriptional machinery (1). In addition, the Swi/Snf class of proteins can form complexes that can have a profound affect on chromatin structure and gene expression (2). Genetic and biochemical studies have demonstrated that these Swi/Snf proteins can cause ATP-dependent disruption of nucleosome structure at a promoter and enhance the binding of transcription factors to their binding sites (2). The action of these proteins can also lead to nucleosome movement and changes in chromatin conformation, resulting in transcriptional activation (or repression) of a gene or region.

CHD (Chromodomain, Helicase, DNA-binding) genes (3) encode a novel class of Swi/Snf proteins which is characterized by the presence of a Swi/Snf-like helicase-ATPase domain, a DNA binding domain, and a chromodomain motif that can directly effect chromatin structure and gene transcription. Of the four known members of this gene family in humans (CHD1-CHD4) (3), two have been shown to participate in multiprotein complexes responsible for chromatin remodeling. The NuRD (for Nucleosome Remodeling and histone Deacetylation) complex (originally known as Mi2) is a ~2 MDa complex that consists of at least seven proteins, but the key functional protein in these complexes appears to be either Mi-2a or Mi-2b. Mi-2a is now known as CHD3 and Mi-2b is known as CHD4. There is increasing evidence that CHD protein complexes can have a profound effect on chromatin structure and gene expression, and are thus likely to play an important role in regulating development, cell cycle control, and oncogenesis.

SUMMARY OF THE INVENTION

A novel member of the CHD gene family, designated CHD5, is identified herein. The encoded CHD5 protein comprises chromodomain, helicase and DNA binding motifs. The CHD5 protein exhibits a particularly high degree of homology to the CHD3 and CHD4 proteins. Of note, the CHD5 gene is preferentially expressed in total brain, fetal brain and cerebellum, as well as in the adrenal gland. The CHD5 gene maps to chromosomal region 1p36.3. This portion of chromosome 1 is frequently deleted in a variety of cancers including human neuroblastomas (4-7). The expression pattern of CHD5 and homology to the CHD family of proteins which are known to be involved in maintenance and regulation of chromatin structure and transcriptional regulation, and the correlation between neuroblastoma and deletion of this gene, demonstrates that CHD5 implicates as a modulator of normal neural development and neoplasia of neural tissue origin.

The present invention relates to the identification of novel nucleic acid molecules and proteins encoded by such nucleic acid molecules or variants thereof, that participate in maintenance and regulation of chromatin structure, gene transcription, and oncogenesis.

According to one aspect of the invention, an isolated nucleic acid molecule is provided which includes a complete coding region for a human Chromodomain, Helicase, DNA-binding 5 (CHD5) protein of a predicted size between about 200 to 250 kilodaltons. The CHD5 protein is preferably about 223 kilodaltons. Analysis of the amino acid sequence reveals that the CHD5 protein comprises two $NH_2$-terminal zinc finger domains of the plant homeodomain (PHD) class and two chromodomains, a central region which includes a predicted DEAH-box-type helicase domain and a putative SNF2 domain, and several nuclear localization signals. The DEAH box is a conserved motif, comprised of the amino acid sequence Asp-Glu-Ala-His (DEAH; amino acids 847-850 of SEQ ID NO: 2), which is present in the helicase domain of a subclass of putative DNA/RNA helicases.

In yet another embodiment of the invention, an isolated nucleic acid molecule encoding a CHD5 protein is provided. In a particularly preferred embodiment, the CHD5 protein has an amino acid sequence the same as SEQ ID NO: 2. An exemplary CHD5 encoding nucleic acid molecule of the invention comprises SEQ ID NO: 1.

According to another aspect of the present invention, an isolated nucleic acid molecule is provided, which has a sequence selected from the group consisting of: (1) SEQ ID NO: 1; (2) a sequence specifically hybridizing with preselected portions or all of the complementary strand of SEQ ID NO: 1; (3) a sequence encoding preselected portions of a polypeptide having the sequence of SEQ ID NO: 2; (4) a sequence encoding part or all of a polypeptide having amino acid SEQ ID NO: 2. Such partial sequences are useful as probes to identify and isolate homologues of the CHD5 gene of the invention. Accordingly, isolated nucleic acid sequences encoding natural allelic variants of SEQ ID NO: 2 are also contemplated to be within the scope of the present invention. The term natural allelic variants will be defined hereinbelow.

In yet another embodiment of the present invention, primers suitable for amplifying CHD5 encoding nucleic acids are provided in Table I. The present invention also encompasses CHD5-specific PCR primers which share at least about 80% homology with the primers listed in Table I.

CHD5 polypeptides may conveniently be obtained by introducing expression vectors into host cells in which the vector is functional, culturing the host cells so that the CHD5 polypeptides are produced and recovering the CHD5 polypeptides from the host cells or the surrounding medium. Vectors comprising nucleic acids according to the present invention and host cells comprising such vectors or nucleic acids form further aspects of the present invention.

In a further embodiment the CHD5 protein may be encoded by natural allelic variants of SEQ ID NO: 1. The invention also encompasses variants having 95% identity to SEQ ID NO: 1. Inasmuch as certain amino acid variations may be present in CHD5 protein encoded by aforementioned natural allelic variants, such proteins are also contemplated to be within the scope of the invention.

According to another aspect of the invention, antibodies immunologically specific for the proteins described hereinabove are provided. Such antibodies may be monoclonal or polyclonal. Additionally antibody fragments having binding affinity for CHD5 are provided. Such antibody fragments comprise Fab, Fab', F(ab')2, F(v) and Sfv generated recombinantly. The anti-CHD5 antibodies or fragments thereof may be used to advantage in the immunoassays and kits described below.

In yet a further aspect of the invention, methods are provided for generating fusion proteins comprising a nucleotide sequence encoding a desired protein sequence linked in frame to nucleic acids encoding CHD5. Methods are also disclosed for detecting CHD5-fusion proteins within cells.

The nucleic acids, proteins/polypeptides, peptides and antibodies of the present invention may be used to advantage for a variety of applications related to basic and clinical research.

In a further aspect of the present invention, there is provided a kit for generating CHD5 protein, fragments thereof, or CHD5 fusion proteins, the kit comprising one or more nucleic acid vectors which can be engineered to express CHD5, a CHD5 fragment thereof, or a CHD5 fusion protein in cell types suited for expression studies. Examples of cell types well-suited for expression studies include, but are not limited to: bacteria, yeast, insect, and mammalian cells. Other expression systems are also contemplated and are well known to those of skill in the art. The kit will also comprise one or more antibodies capable of specifically binding and/or detecting the CHD5 protein, fragment thereof, or CHD5 component of a CHD5 fusion protein.

In a preferred embodiment of the invention, molecular markers are provided for monitoring cancer initiation and/or progression in patients who are most at risk for neuroblastoma or other tumor with chromosome (1p) deletions and would benefit from definitive diagnosis. Early diagnosis provides for immediate and appropriate therapeutic intervention (e.g., chemotherapy, radiation therapy, surgical resection, or combinations of the above). As described herein, mutations and/or deletions to the nucleic acid encoding CHD5 are correlated with the presence of neuroblastoma. Thus, methods for delineating such alterations in CHD5 nucleic acid sequences provides means to detect the presence of neuroblastoma in a patient or a biological sample derived from a patient. Moreover, as described herein, a reduction and/or loss of CHD5 protein or CHD5 activity is also correlated with the presence of neuroblastoma. Accordingly, methods for measuring CHD5 protein levels and/or activity are also provided herein to facilitate detection of the presence of neuroblastoma in a patient or a biological sample derived from a patient.

Accordingly, the present invention includes methods, compositions and kits which employ one or more detection reagents comprising an antibody which binds specifically with CHD5 protein and a CHD5-specific PCR primer pair for determining CHD5 expression levels in a cancer (e.g., a tumor) in a mammal. In the clinical setting, the cancer is generally of neural origin. Additionally, the methods, compositions and kits of the invention are useful in the diagnosis and treatment of such cancers and tumors in a mammal.

The present invention is directed to methods for detecting a cancer (e.g., a tumor) in a biological sample. An exemplary method entails contacting a biological sample with a composition comprising at least one CHD5-specific detection reagent for a suitable time period and in an amount effective for detection of a CHD5-associated molecule in a sample; determining the amount of the CHD5-associated molecule; the method optionally further comprising, for example, histological analysis, Flow cytometry, nucleic acid analysis, e.g. PCR, RFLP etc., and pathological assessment of a cancer; thereby diagnosing the tumor present in a biological sample.

Exemplary CHD5-detection reagents include without limitation, oligonucleotides which hybridize with CHD5 encoding nucleic acids, and antibodies or fragments thereof with binding affinity for CHD5 polypeptides or fragments thereof. Such antibody fragments include sFv, and Fab for example. Exemplary CHD5-associated molecules are genomic DNA, cDNA, or mRNA or oligonucleotides encoding CHD5 protein or fragments or complementary strands thereof and CHD5 polypeptides and fragments thereof.

In an exemplary method PCR is employed to amplify CHD5 sequence. Suitable primers for use in the method have a sequence selected from the group consisting of the primers provided in Table I. Suitable methods for characterizing the reaction product include, without limitation, gel electrophoresis, restriction digest mapping, scintillation counting and filter paper assays.

In another embodiment of the invention, CHD5 polypeptides or fragments thereof may be further analyzed using methods which include without limitation, flow cytometric analysis, immunochemical detection or localization and immunoblot analysis. Suitable biological samples include without limitation, neuroblastoma tissue, adrenal gland tissue, and neural tissue.

The present invention also includes a method of treating a cancer in a mammal, the method comprising administering to a mammal a composition comprising a CHD5-associated molecule in a therapeutically effective amount to restore CHD5 activity in cancer cells, thereby re-establishing CHD5-mediated transcriptional repression in the cancer cells in said mammal. Cancers to be treated may be of neural origin, including without limitation neuroblastoma, medulloblastoma, oligodendroglioma, meningioma, glioblastoma, neuroendocrine tumors, ependymomas, astrocytomas, gliomas. Such tumors often harbor hemizygous deletions of CHD5 and the surrounding 1p36 region. Non-neuronal tumors that are characterized by 1p36 deletions such as, but not limited to, breast cancer, colon cancer, liver tumors and germ cell tumors may also be treated using the methods of the present invention.

Pharmaceutical compositions suitable for administration to a patient comprising the above-mentioned CHD5-associated molecules are also within the scope of the present invention.

In yet another aspect, the present invention also provides kits for diagnosing a cancer in a mammal. An exemplary kit contains a container or a sample vial for storing a sample of a tissue or a body fluid; a composition comprising at least one CHD5-specific detection reagent in an amount effective to permit detection of a CHD5-associated molecule in a sample; and an instructional material which directs use of the composition for determining the amount of a CHD5-associated molecule.

In another embodiment of the invention, additional molecular markers are provided for monitoring cancer initiation and/or progression in patients who are most at risk for neuroblastoma and would benefit from definitive diagnosis. As described herein, mutations and/or deletions to the nucleic acid sequence of human chromosome 1p36.3 are correlated with the presence of neuroblastoma. This region comprises ten genes (including the CHD5 gene) which are additional markers for the 1p deletion in neuroblastomas. These include four (4) genes identified to date that localize to 1p36.3, KCNAB2, RPL22, ICMT, and HBACH. Thus, methods for delineating alterations in KCNAB2, RPL22, ICMT, and HBACH sequences are encompassed by the present invention and provide means to detect the presence of neuroblastoma in a patient or a biological sample derived from a patient. Such alterations include, but are not limited to, loss of heterozygosity, mutations, and polymorphisms of the above genes.

Aspects and embodiments of the present invention will now be illustrated, by way of example, with reference to the accompanying figures. Further aspects and embodiments will be apparent to those skilled in the art.

DETAILED DESCRIPTION OF THE INVENTION

Figure 1:
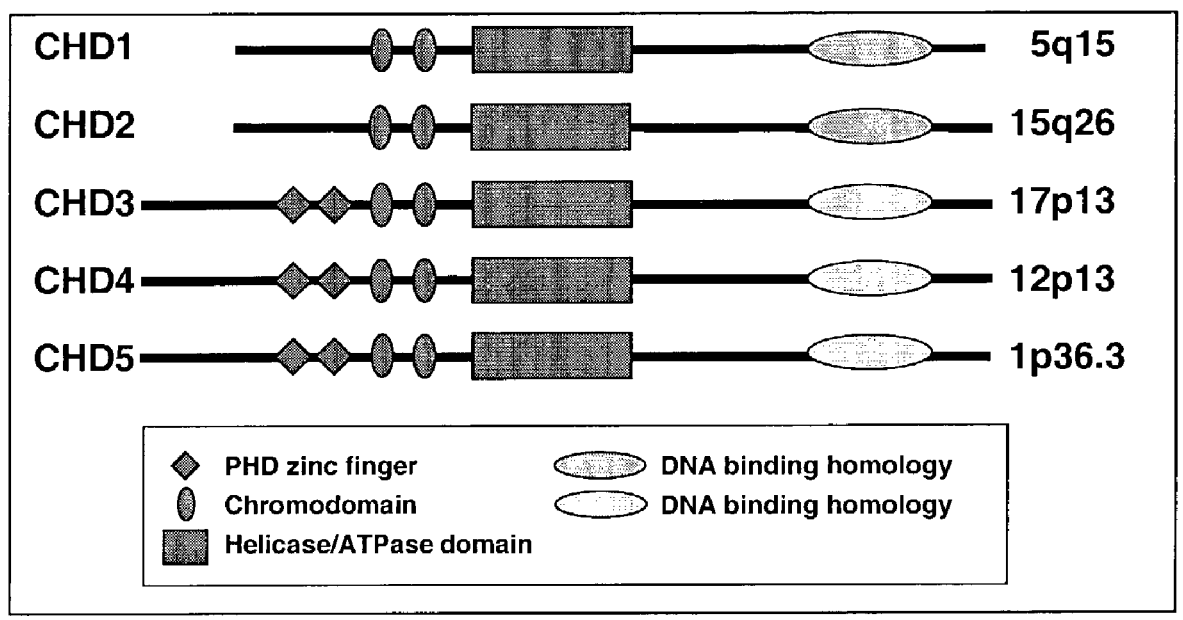
FIG. 1 is a diagram showing a comparison of the structural motifs of the human CHD proteins and the chromosomal localization of the CHD family genes. Shown are the structures of the four previously described human CHD proteins (CHD1-4) and the shared motifs compared to the protein sequences for the CHD5 protein described herein. Also shown are the chromosomal locations of the genes encoding these proteins. Adapted from Woodage (3).

The present invention relates generally to the fields of human genetics and CHD proteins. Specifically, the present invention provides nucleic acid sequences (SEQ ID NO: 1) encoding full length CHD5 protein (SEQ ID NO: 2), and antibodies immunologically specific for CHD5. The invention further provides methods for screening patient samples to determine whether a patient has a predisposition to or has a disorder related to aberrant CHD5 protein activity. Finally, the invention provides methods for identifying mutations in the CHD5 gene, which are useful for diagnosing CHD5-associated pathological disorders.

Provided herein is the first disclosure of a nucleic acid sequence (SEQ ID NO: 1) encoding a new member of the human CHD protein family, designated CHD5 (SEQ ID NO: 2). Chromodomain proteins are known to regulate gene expression in a developmentally restricted and gene-specific manner and likely confer the specificity of their transcriptional repression through the recruitment of other effector proteins. Such proteins may then bind to the promoters of other genes and target histone deacetylation and transcriptional repression to these genes or chromatin regions. The preferential expression of CHD5 in neural tissues and the adrenal glands suggests that CHD5 may play an important role in the development of the nervous system. Moreover, since CHD5 maps to a region that is frequently deleted in neuroblastomas and other neural crest tumors, deletion of CHD5 may contribute to malignant transformation in these and other neuronal cancers.

As described in Example I, the expression pattern of human CHD5 was determined in a plurality of tissues. Analysis of the CHD5 expression pattern provides information critical for the assessment of the role of CHD5 protein in the regulation of transcription and chromatin structure in different tissue and cell types.

The full length DNA sequence (SEQ ID NO: 1) is comprised of 9646 bp and includes the entire open reading frame (ORF) of the CHD5 protein. The initiation site was assigned to the first ATG codon at nucleotide position 101. The protein comprises 1954 amino acids (SEQ ID NO: 2) and has a molecular weight of approximately 223 kDa.

The present inventors have cloned the full length CHD5 gene (SEQ ID NO: 1), which encodes a novel human CHD protein (SEQ ID NO: 2). As shown herein, CHD5 is expressed specifically in tissues of neural origin. Notably, the CHD5 gene has been localized to the 1p36.3 region of chromosome 1 which is frequently deleted in neuroblastomas, wherein the expression of CHD5 is dramatically reduced. Accordingly, the present inventors have discovered a functional correlation between a loss of CHD5 expression and the development of neuroblastoma. In accordance with the present invention, methods are provided for the expression of CHD5 in recombinant host cells. Also provided are methods for the use of such recombinant host cell systems to screen for mutations in CHD5 that contribute to tumorigenic progression. The identification of CHD5 mutations which lead to aberrant CHD5 protein activity in recombinant host cells and/or in vivo provide diagnostic indicators which can be used to advantage to detect neuroblastoma onset and/or progression and developmental disorders of the nervous system. Methods are also provided to screen for compounds capable of modulating CHD5 activity.

The present invention also provides isolated antibodies, preferably monoclonal antibodies, which specifically bind to an isolated polypeptide comprised of at least five amino acid residues encoded by the CHD5 locus.

In accordance with the present invention, reduced or undetectable levels of CHD5 expression have been observed in neuroblastoma cell lines. Thus, methods assaying CHD5 expression are provided for diagnosing patients suspected of having neuroblastoma.

Detection of CHD5 in tumor samples may be performed by various methods commonly known to those skilled in the art. In one aspect of the present invention, methods of use are provided for diagnosing cancers of the nervous system (e.g., neuroblastoma) by screening for CHD5 expression. Such diagnostic methods include without limitation RT-PCR techniques as well as immunospecific methods for the detection of CHD5 associated antigens.

Also provided by the present invention are methods of detecting a polynucleotide comprising a portion of the CHD5 locus or its expression product in an analyte. Such methods may further comprise the step of amplifying the portion of the CHD5 locus, and may further include a step of providing a set of polynucleotides which are primers for amplification of said portion of the CHD5 locus.

The present invention also provides methods for screening the CHD5-encoding nucleic acid to identify mutations. Such methods may further comprise the step of amplifying a portion of the CHD5 locus, and may further include a step of providing a set of polynucleotides which are primers for amplification of said portion of the CHD5 locus. Exemplary primers are set forth in Table I. Exemplary primer pairs for applications such as PCR are provided in Table I, under the SSCP heading. The method is useful for identifying mutations for use in either determination of a predisposition to a CHD5 associated disorder or a diagnosis of such a disorder.

The following description sets forth the general procedures involved in practicing the present invention. To the extent that specific materials are mentioned, it is merely for purposes of illustration and is not intended to limit the invention. Unless otherwise specified, general cloning and gene expression procedures, such as those set forth in Current Protocols in Molecular Biology, Ausubel et al. eds., J W Wiley and Sons, NY (1998) and Molecular Cloning A Laboratory Manual, Third Edition, Sambrook et al. eds., Cold Spring Harbor Laboratory Press (2001) are utilized.

I. Definitions

Various terms relating to the biological molecules of the present invention are used hereinabove and also throughout the specifications and claims.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 75%, but often, more than 90%, of the nucleotides of the sequence are identical over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

The present invention also includes methods of use for active portions, fragments, derivatives and functional or non-functional mimetics of CHD5 polypeptides or proteins of the invention. An "active portion" of CHD5 polypeptide means a peptide that is less than the full length CHD5 polypeptide, but which retains measurable biological activity.

A "fragment" or "portion" of the CHD5 polypeptide means a stretch of amino acid residues-of at least about five to seven contiguous amino acids, often at least about seven to nine contiguous amino acids, typically at least about nine to thirteen contiguous amino acids and, most preferably, at least about twenty to thirty or more contiguous amino acids. Fragments of the CHD5 polypeptide sequence, antigenic determinants, or epitopes are useful for eliciting immune responses to a portion of the CHD5 amino acid sequence.

A "derivative" of the CHD5 polypeptide or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, and may or may not alter the activity of the original CHD5 polypeptide.

As mentioned above, the CHD5 polypeptide or protein of the invention includes any analogue, fragment, derivative or mutant which is derived from a CHD5 polypeptide and which retains at least one property or other characteristic of the CHD5 polypeptide. Different "variants" of the CHD5 polypeptide exist in nature. These variants may be alleles characterized by differences in the nucleotide sequences of the gene coding for the protein, or may involve different RNA processing or post-translational modifications. A skilled person can produce variants having single or multiple amino acid substitutions, deletions, additions or replacements. These variants may include inter alia: (a) variants in which one or more amino acid residues are substituted with conservative or non-conservative amino acids, (b) variants in which one or more amino acids are added to the CHD5 polypeptide, (c) variants in which one or more amino acids include a substituent group, and (d) variants in which the CHD5 polypeptide is fused with another peptide or polypeptide such as a fusion partner, a protein tag or other chemical moiety, that may confer useful properties to the CHD5 polypeptide, such as, for example, an epitope for an antibody, a polyhistidine sequence, a biotin moiety and the like. Other CHD5 polypeptides of the invention include variants in which amino acid residues from one species are substituted for the corresponding residues in another species, either at the conserved or non-conserved positions. In another embodiment, amino acid residues at non-conserved positions are substituted with conservative or non-conservative residues. The techniques for obtaining these variants, including genetic (suppressions, deletions, mutations, etc.), chemical, and enzymatic techniques are known to the person having ordinary skill in the art.

To the extent such allelic variations, analogues, fragments, derivatives, mutants, and modifications, including alternative nucleic acid processing forms and alternative post-translational modification forms result in derivatives of the CHD5 polypeptide that retain any of the biological properties of the CHD5 polypeptide, they are included within the scope of this invention.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the basic and novel functional characteristics of the sequence.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and the method used. For example, for diagnostic applications, depending on the complexity of the target sequence, the oligonucleotide probe typically contains 15-25 or more nucleotides, although it may contain fewer nucleotides. The probes herein are selected to be "substantially" complementary to different strands of a particular target nucleic acid sequence. Such probes must, therefore, be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

Amino acid residues described herein are preferred to be in the "L" isomeric form. However, residues in the "D" isomeric form may be substituted for any L-amino acid residue, provided the desired properties of the polypeptide are retained.

All amino-acid residue sequences represented herein conform to the conventional left-to-right amino-terminus to carboxy-terminus orientation.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, to that sequence. Thus, for example, a homopolymer nucleic acid sequence or a nucleic acid sequence complementary to a target oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be attached to proteins to facilitate protein isolation by procedures such as affinity or immunoaffinity chromatography. Chemical tag moieties include such molecules as biotin, which may be added to either nucleic acids or proteins and facilitate isolation or detection by interaction with avidin reagents, and the like. Numerous other tag moieties are known to, and can be envisioned by, the trained artisan, and are contemplated to be within the scope of this definition.

As used herein, the terms "reporter," "reporter system", "reporter gene," or "reporter gene product" shall mean an operative genetic system in which a nucleic acid comprises a gene that encodes a product which when expressed produces a reporter signal that is readily measurable, e.g., by biological assay, immunoassay, radioimmunoassay, or by colorimetric, fluorogenic, chemiluminescent or other method. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, and may include, but not be limited to, such elements as promoters, enhancers, translational control sequences, polyA addition signals, transcriptional termination signals and the like.

The terms "transform", "transfect", and "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like. The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on to or inherited by progeny cells or organisms of the recipient cell or organism. In other applications, the introduced nucleic acid may exist in the recipient cell or host organism only transiently.

A "clone" or "clonal cell population" is a population of cells derived from a single cell or common ancestor by mitosis.

A "cell line" is a clone of a primary cell or cell population that is capable of stable growth in vitro for many generations.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunoglobulin molecule such as those portions known in the art as Fab, Fab', F(ab')2 and F(v).

As used herein, "Chromodomain, Helicase, DNA-binding" or "CHD" activity shall refer to chromatin unwinding, DNA repair and recombination, transcriptional regulation, and modulation of tumorigenesis. Functionally, activity may be determined by measuring chromatin remodeling and/or transcriptional regulation of downstream genes. For example, mononucleosome disruption assays and histone deacetylase assays may be performed to measure chromatin remodeling and reverse transcriptase polymerase chain reaction (RT-PCR), or probing of gene arrays and/or blots may be used to measure changes in transcription of a gene(s) regulated by CHD5 activity. Such methods are described herein and have been described previously. See Example II and references 45, 47-49.

As used herein, the term "tumor suppressor gene or protein" refers to a gene or a protein encoded thereby whose loss or inactivation contributes to the malignant transformation of a cancer (leukemia or solid tumor).

As used herein, the term "neural development regulatory gene or protein" refers to a gene or a protein encoded thereby that plays a critical role in the development of the central or peripheral nervous system.

As used herein, the term "transcriptional regulatory gene or protein" refers to a gene or a protein encoded thereby that binds to and controls the expression of another gene (positively or negatively) by binding to upstream DNA sequences directly or as part of a complex.

As used herein, the term "chromatin remodeling gene or protein" refers to a gene or a protein encoded thereby that binds to DNA directly or as part of a complex and alters the conformation of the DNA. This can be achieved by changing the acetylation of histones or other physical interactions with the DNA to change its conformation and therefore its accessibility to transcriptional complexes (in a positive or negative manner).

II. Preparation of CHD5-Encoding Nucleic Acid Molecules, CHD5 Proteins and Antibodies Thereto A full length cDNA sequence encoding a novel human CHD protein, designated herein as CHD5, has been isolated. The cDNA was derived from mRNA isolated from fetal brain cells. The CHD5 protein is a member of the CHD family of proteins, which are known to be involved in the regulation of chromatin structure and gene transcription. As such the molecule may be exploited for the purpose of examining its role in modulation of expression of downstream genes. CHD5 expression systems, both naturally occurring and engineered, can be used to determine a gene signature or profile of downstream genes whose expression is modulated (up-regulated or down-regulated) as a consequence of alterations in CHD5 activity. Such information is particularly useful when evaluating the causative role that changes in CHD5 activity levels may play in a variety of disorders, including cancer. Nucleic acid sequences encoding full length human CHD5 are provided herein as SEQ ID NO: 1. The amino acid sequence of full length CHD5 is provided herein as SEQ ID NO: 2. Analysis of the CHD5 amino acid sequence reveals the presence of two $NH_2$-terminal zinc finger domains of the PHD class and two chromodomains, a central region which includes a predicted DEAH-box-type helicase domain and a putative SNF2 domain, and several nuclear localization signals.

A. Nucleic Acid Molecules

Nucleic acid molecules encoding CHD5 may be prepared by two general methods: (1) they may be synthesized from appropriate nucleotide, or (2) they may be isolated from biological sources. Both methods utilize protocols well known in the art.

The availability of nucleotide sequence information, such as full length cDNA having SEQ ID NO: 1 enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a large double-stranded DNA molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct the entire protein encoding sequence. A synthetic DNA molecule so constructed may then be cloned and amplified in an appropriate vector.

Nucleic acid sequences encoding CHD5 may be isolated from appropriate biological sources using methods known in the art. In a preferred embodiment, a cDNA clone is isolated from an expression library of human origin. In an alternative embodiment, genomic clones encoding CHD5 may be isolated. Alternatively, cDNA or genomic clones coding homology CHD5 protein may be isolated from other species, such as other vertebrates or mammals, using oligonucleotide probes corresponding to predetermined sequences within the CHD5 gene.

In accordance with the present invention, nucleic acids having the appropriate level of sequence homology with the protein coding region of SEQ ID NO: 1 may be identified by using hybridization and washing conditions of appropriate stringency. For example, hybridizations may be performed, according to the method of Sambrook et al., (supra) using a hybridization solution comprising: 5×SSC, 5× Denhardt's reagent, 0.5-1.0% SDS, 100 μg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 0.5-1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules of a specified sequence homology is (Sambrook et al., 1989):

$$T_m = 81.5° C. + 16.6 \text{ Log}[Na+] + 0.41(\% G+C) - 0.63(\% \text{ formamide}) - 600/\#bp \text{ in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

Nucleic acids of the present invention may be maintained as DNA in any convenient cloning vector. In a preferred embodiment, clones are maintained in plasmid cloning/expression vector, such as pBluescript (Stratagene, La Jolla, Calif.), which is propagated in a suitable E. coli host cell.

CHD5-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having SEQ ID NO: 1. Such oligonucleotides are useful as agents to inhibit or augment CHD5 activity in cells or tissues. In particular, the present invention describes the use of CHD5 encoding nucleic acids in histone deacetylase and nucleosome remodeling assays, wherein the effects of test agents on modulating and/or restoring CHD5 expression can be assessed (as described in Example II). In another preferred embodiment, the present invention describes the use of CHD5 encoding nucleic acids to restore expression of CHD5 protein in the context of a cancer cell (e.g., neuroblastoma tumor cell), wherein the effect of CHD5 expression may be measured by assaying the tumorigenic potential of the cancer cell (as described in Example III).

The CHD5-encoding nucleic acids of the invention may also be used to identify genes encoding proteins that interact with CHD5 proteins (e.g., by the "interaction trap" technique), which should further accelerate identification of the components involved in CHD5 mediated transcriptional regulation and chromatin structure. The CHD5 encoding nucleic acids may also be used to generate primer sets suitable for PCR amplification of target CHD5 DNA. See Table I. Criteria for selecting suitable primers are well known to those of ordinary skill in the art.

TABLE I

Primers for PCR Amplification of Target CHD5 DNA

| 1st PCR (templates) | Primer pair name/ID | Primer sequence 1 | | Orien-tation | cDNA start | cDNA finish | genomic start | genomic finish | cDNA size | genomic size | Exon(s) spanned |
|---|---|---|---|---|---|---|---|---|---|---|---|
| RT-PCR | CHD5-BIO#5 | AGGATTACCACACGCTGACC | (SEQ ID NO: 8) | + | 558 | 577 | 348408 | 348427 | 273 | 273 | 4-5 |
| Southern | CHD5-BIO#6 | GTCTTGGCCTTGCGGATAG | (SEQ ID NO: 9) | - | 813 | 831 | 349363 | 349381 | | | |
| RT-PCR | CHD5-BIO#7 | AAGAAGCTGAGGGACGACAA | (SEQ ID NO: 10) | + | 2090 | 2109 | 360179 | 360198 | 299 | 1601 | 13-15 |
| Southern | CHD5-BIO#8 | GTTGATGATGGTGGAGAGGG | (SEQ ID NO: 11) | - | 2370 | 2389 | 361761 | 361780 | | | |
| RT-PCR | CHD5-BIO#1 | TCATCTACGACTCGGACTGGAACC | (SEQ ID NO: 12) | + | 3447 | 3470 | 373811 | 373834 | 333 | 1695 | 22-24 |
| Southern | CHD5-BIO#2 | CCTTTGGAGGACTGGACATCAG | (SEQ ID NO: 13) | - | 3759 | 3780 | 375485 | 375506 | | | |
| RT-PCR | CHD5-BIO#3 | AAGATGACGAGGGGAAGAAGGAGG | (SEQ ID NO: 14) | + | 5163 | 5186 | 391838 | 391861 | 345 | 2252 | 35-38 |
| Southern | CHD5-BIO#4 | TCAATGACCAACGCCTGCTC | (SEQ ID NO: 15) | - | 5489 | 5508 | 394071 | 394090 | | | |
| Southern | CHD5-BIO#5 | AGGATTACCACACGCTGACC | (SEQ ID NO: 16) | + | 558 | 577 | 348408 | 348427 | 1194 | 9285 | 4-11 |
|  | CHD5#10 | GGCTCATCCATGTCGTTCTT | (SEQ ID NO: 17) | - | 1733 | 1752 | 357674 | 357693 | | | |
| Whole cDNA | CHD5#16 | GCAGCGCACGGGGTTAAGG | (SEQ ID NO: 18) | + | 25 | 42 | 323956 | 323973 | 5916 | 73688 | 1-40 |
|  | CHD5#18 | CGCCCACCTCCCCTCCTC | (SEQ ID NO: 19) | - | 71 | 88 | 324002 | 324019 | 5870 | 73642 | 1-40 |
|  | CHD5#27 | CAGGGGCATCTGGTTGTAGT | (SEQ ID NO: 20) | - | 5922 | 5941 | 397625 | 397644 | | | |
| TAQMAN | CHD5F | CCGAGATCCAAACGGT | (SEQ ID NO: 21) | + | 1443 | 1459 | 355161 | 355177 | 82 | 2064 | 11-12 |
|  | CHD5R | CCAGTGTAGAATCCGCTGGAC | (SEQ ID NO: 22) | - | 1505 | 1525 | 357205 | 357225 | | | |
|  | CHD5PROBE | CTCTGCCCGCGTGTACTTGCC | (SEQ ID NO: 23) | + | 1466 | 1487 | 355184 | 355201 | | | |
| SEQUENCING | CHD5#9 | CTTCAGAACAACCTGGAGGA | (SEQ ID NO: 24) | + | 2735 | 2754 | 367477 | 367496 | | | |
| SEQUENCING | CHD5#33 | ATCTCCTCGGGCAACAGC | (SEQ ID NO: 25) | - | 139 | 156 | 324070 | 324087 | | | |
| 5'RACE | GSP1-3 | TCATCATTGCTCCCCTCTTT | (SEQ ID NO: 26) | - | 302 | 321 | 335900 | 335921 | | | |
|  | GSP2-4 | TTCTTCCCGCTTCCCTTTACA | (SEQ ID NO: 27) | - | 281 | 300 | 335879 | 335898 | | | |
| SSCP | #18/#6 CHD5-BIO#18 | CGCCCACCTCCCCTCCTC | (SEQ ID NO: 28) | + | 71 | 88 | 324002 | 324019 | 264 | 20563 | 1-3 |
|  | CHD5-BIO#5'.1R | TTCTCTGATAGCTCATCATTGC | (SEQ ID NO: 29) | - | 312 | 333 | 344565 | 344544 | | | |
|  | #18/#6 CHD5-BIO#5'.2F | GTGTAAAGGGAAGCGGAAGA | (SEQ ID NO: 30) | + | 280 | 299 | 335878 | 335878 | 318 | 12569 | 2-4 |

TABLE I-continued

Primers for PCR Amplification of Target CHD5 DNA

| 1st PCR (templates) | Primer pair name/ID | Primer sequence 1 | | Orien-tation | cDNA start | cDNA finish | genomic start | genomic finish | cDNA size | genomic size | Exon(s) spanned |
|---|---|---|---|---|---|---|---|---|---|---|---|
| | CHD5-BIO#5'.2R | TGGCTGAAGGCCTTGTAGTT | (SEQ ID NO: 31) | - | | | 348447 | 348428 | | | |
| #5/#8 | CHD5-BIO#5 | AGGATTACCACACGCTGACC | (SEQ ID NO: 32) | + | 578 | 597 | 348808 | 348427 | 274 | 973 | 4-5 |
| | CHD5-BIO#6 | GCTTTGGCCTTGCGGATAG | (SEQ ID NO: 33) | - | 558 | 577 | 349381 | 349363 | | | |
| #5/#8 | CHD5-BIO#02F | GCCGGCTGAGAGACGGTCA | (SEQ ID NO: 34) | + | 828 | 813 | 349293 | 349311 | 408 | 5406 | 5-8 |
| | CHD5-BIO#02R | GCTGGCACACCTCACAGTAA | (SEQ ID NO: 35) | - | 743 | 761 | 354699 | 354680 | | | |
| #5/#8 | CHD5-BIO#PHD 2.F | TGGTGACGGCTATGAGACAG | (SEQ ID NO: 36) | + | 1132 | 1151 | 354650 | 354669 | 253 | 422 | 8-9 |
| | CHD5-BIO#PHD 1.R | GAACTCCATGTGTCGTCCT | (SEQ ID NO: 37) | - | 1102 | 1121 | 355072 | 355053 | | | |
| #5/#8 | CHD5-BIO#PHD 2.F2 | AGGACGACGATGAAGAG | (SEQ ID NO: 38) | + | 1335 | 1354 | 355008 | 355027 | 247 | 2228 | 9-10 |
| | CHD5-BIO#PHD 2.R | TCCGTCCACCTCCAGTGTA | (SEQ ID NO: 39) | - | 1290 | 1309 | 357236 | 357218 | | | |
| #5/#8 | CHD5-BIO#10F | GAGATCCCAAACGGTGAATG | (SEQ ID NO: 40) | + | 1518 | 1536 | 355163 | 355182 | 308 | 2530 | 9-11 |
| | CHD5-BIO#10 | GGCTCATCCATGTCGTTCTT | (SEQ ID NO: 41) | - | 1445 | 1464 | 357693 | 357674 | | | |
| #5/#8 | CHD5-BIO#Chr omo.F2 | CACGGTGATGTATCGCAACT | (SEQ ID NO: 42) | + | 1733 | 1752 | 357646 | 357665 | 405 | 2552 | 11-13 |
| | CHD5-BIO#Chr omo.R1 | TTGTCGTCCCTCAGCTTCTT | (SEQ ID NO: 43) | - | 1705 | 1724 | 360198 | 360179 | | | |
| #5/#8 | CHD5-BIO#SNF 2.1F | CAAGAGGCTGCTCAAGAGG | (SEQ ID NO: 44) | + | 2090 | 2109 | 360157 | 360176 | 322 | 1623 | 13-15 |
| | CHD5-BIO#8 | GTTGATGATGGTGGAGAGGG | (SEQ ID NO: 45) | - | 2068 | 2087 | 361780 | 361761 | | | |
| #7/#2 | CHD5-BIO#7 | AAGAAGCTGAGGGACGACAA | (SEQ ID NO: 46) | + | 2090 | 2109 | 360179 | 360198 | 349 | 1650 | 13-15 |
| | CHD5-BIO#SNF 2.1R | AGGTGACCACGTAGAAGTCG | (SEQ ID NO: 47) | - | 2419 | 2438 | 361829 | 361810 | | | |
| #7/#2 | CHD5-BIO#SNF 2.2F | CCCTCTCCACCATCATCAAC | (SEQ ID NO: 48) | + | 2370 | 2389 | 361761 | 361780 | 426 | 5776 | 15-17 |
| | CHD5-BIO#SNF 2.2R | TGAACCTCTCTGGAGTCAGGA | (SEQ ID NO: 49) | - | 2775 | 2795 | 367537 | 367517 | | | |

TABLE I-continued

Primers for PCR Amplification of Target CHD5 DNA

| 1st PCR (templates) | Primer pair name/ID | Primer sequence 1 | | Orientation | cDNA start | cDNA finish | genomic start | genomic finish | cDNA size | genomic size | Exon(s) spanned |
|---|---|---|---|---|---|---|---|---|---|---|---|
| #7/#2 | CHD5-BIO#SNF2.3F | AGAACAACCTGGAGGAGCTG | (SEQ ID NO: 50) | + | 2739 | 2758 | 367481 | 367500 | 412 | 2352 | 17-19 |
| | CHD5-BIO#SNF2.3R2 | CTTCCATCGTAGGAGCCATT | (SEQ ID NO: 51) | - | 3131 | 3150 | 369833 | 369814 | | | |
| #7/#2 | CHD5-BIO#Helicase.F2 | ACCCCTACCTCTTCCCTGTG | (SEQ ID NO: 52) | + | 3084 | 3103 | 369309 | 369328 | 410 | 4543 | 19-23 |
| | CHD5-BIO#Helicase.R2 | GAAGGCTGGATGTCATTGT | (SEQ ID NO: 53) | - | 3474 | 3493 | 373852 | 373838 | | | |
| #1/#4 | CHD5-BIO#1 | TCATCTACGATCGACTGGAACC | (SEQ ID NO: 54) | + | 3447 | 3470 | 373811 | 373834 | 334 | 1695 | 22-24 |
| | CHD5-BIO#2 | CCTTTGGAGGACTGGACATCAG | (SEQ ID NO: 55) | - | 3759 | 3780 | 375506 | 375485 | | | |
| #1/#4 | CHD5-BIO#A | GAGGGCATGATGTCTCAGG | (SEQ ID NO: 56) | + | 3716 | 3734 | 375445 | 375460 | 355 | 1930 | 23-26 |
| | CHD5-BIO#B | GCAGCTTCTCCCAGTAGTCG | (SEQ ID NO: 57) | - | 4051 | 4070 | 377375 | 377356 | | | |
| #1/#4 | CHD5-BIO#C | GGGAAATCATCAAGACAGAG | (SEQ ID NO: 58) | + | 4017 | 4036 | 377322 | 377341 | 344 | 1209 | 26-28 |
| | CHD5-BIO#D | CTCGATGTTGCCACCAACT | (SEQ ID NO: 59) | - | 4342 | 4360 | 378531 | 378513 | | | |
| #1/#4 | CHD5-BIO#E | GGAGGCGCTGAAGAGTGAC | (SEQ ID NO: 60) | + | | | 378461 | 378480 | 339 | 1066 | 28-30 |
| | CHD5-BIO#F | CTAGTGACATGACCCCGATG | (SEQ ID NO: 61) | - | 4609 | 4628 | 379527 | 379508 | | | |
| #1/#4 | CHD5-BIO#G | GTGCAGAGACCTTCGCAGAC | (SEQ ID NO: 62) | + | 4545 | 4564 | 379444 | 379463 | 382 | 3420 | 30-33 |
| | CHD5-BIO#H | TCGTGCTTGTCCTCACTCTC | (SEQ ID NO: 63) | - | 4907 | 4926 | 382864 | 382845 | | | |
| #1/#4 | CHD5-BIO#I | AAGGCAGCCCCCTGGAAGT | (SEQ ID NO: 64) | + | 4858 | 4875 | 382540 | 382557 | 393 | | 32-36 |
| | CHD5-BIO#J | GTGTGCAACTCCGTGAAGC | (SEQ ID NO: 65) | - | 5232 | 5250 | | | | | |
| #3/#26 | CHD5-BIO#3 | AAGATGACGAGGGGAAGAAGGAGG | (SEQ ID NO: 66) | + | 5163 | 5186 | 391838 | 391861 | 346 | 2252 | 35-38 |
| | CHD5-BIO#4 | TCAATGACCAACGCCTGCTC | (SEQ ID NO: 67) | - | 5489 | 5508 | 394090 | 394071 | | | |
| #3/#26 | CHD5-BIO#3 | AAGATGACGAGGGGAAGAAGGAGG | (SEQ ID NO: 68) | + | 5163 | 5186 | 391838 | 391861 | 1046 | 6986 | 35-42 |
| | CHD5-BIO#26 | GGGGCAACGCTGTGTGAAG | (SEQ ID NO: 69) | - | 6189 | 6208 | 398824 | 398805 | | | |

Nucleic acid molecules, or fragments thereof, encoding CHD5 genes may also be utilized to control the production of CHD5 proteins, thereby regulating the amount of protein available to participate in CHD5 mediated transcriptional regulation and chromatin structure. Antisense oligonucleotides corresponding to essential processing sites in CHD5-encoding mRNA molecules may be utilized to inhibit CHD5 production in targeted cells. Alterations in the physiological amount of CHD5 may dramatically affect the ability of this protein to serve as a component of a chromatin complex.

Host cells comprising a CHD5 encoding DNA molecule are encompassed in the present invention. Host cells contemplated for use in the present invention include but are not limited to bacterial cells, fungal cells, insect cells, mammalian cells, and plant cells. The CHD5 encoding DNA molecules may be introduced singly into such host cells or in combination to assess the phenotype of cells conferred by such expression. Methods for introducing DNA molecules are also well known to those of ordinary skill in the art. Such methods are set forth in Ausubel et al. eds., *Current Protocols in Molecular Biology*, John Wiley & Sons, NY, N.Y. 1995, the disclosure of which is incorporated by reference herein.

The availability of CHD5 encoding nucleic acids enables the production of laboratory mice strains carrying part or all of the CHD5 genes or mutated sequences thereof. Such mice may provide an in vivo model for development of neuroblastoma. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo.

The alterations to the 1p36.3 genes (e.g., CHD5) envisioned herein include modifications, deletions, and substitutions. Modifications and deletions render the naturally occurring gene nonfunctional, producing a "knock out" animal. Substitutions of the naturally occurring gene with a homologous gene from a second species results in an animal which produces the gene from the second species. Substitution of the naturally occurring gene for a gene having a mutation results in an animal with a mutated 1p36.3 gene. A transgenic mouse carrying the human CHD5 gene, for example, may be generated by direct replacement of the mouse CHD5 gene with the human CHD5 gene. These transgenic animals are valuable for use in vivo assays for elucidation of medical disorders associated with cellular activities modulated by 1p36.3 genes. A transgenic animal carrying a "knock out" of a nucleic acid of a 1p36.3 gene is useful for the establishment of a nonhuman model in which to investigate the role of 1p36.3 genes (e.g., CHD5) in chromatin structure and regulation of gene expression.

As a means to define the role that CHD5, for example, plays in mammalian systems, mice may also be generated that cannot make CHD5 because of a targeted mutational disruption of the CHD5 gene.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. An altered 1p36.3 gene generally should not fully encode the same 1p36.3 encoded protein native to the host animal and its expression product should be altered to a minor or great degree, or absent altogether. However, it is conceivable that a more modestly modified 1p36.3 gene falls within the compass of the present invention if it comprises a specific alteration.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem (ES) cells. ES cells may be obtained from pre-implantation embryos cultured in vitro. Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated 1p36.3 genes (e.g., CHD5) to selectively inactivate the wild-type gene in totipotent ES cells (such as those described above) and then generate transgenic mice. The use of gene-targeted ES cells in the generation of gene-targeted transgenic mice is known in the art.

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$-fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its nonhomologous insertion with effective herpes drugs such as gancyclovir (GANC) or (1-(2-deoxy-2-fluoro-B-D arabinofluranosyl)-5-iodouracil, (FIAU). By this counter selection, the number of homologous recombinants in the surviving transformants can be increased.

As used herein, a "targeted gene" or "knock-out" is a DNA sequence introduced into the germline or a non-human animal by way of human intervention, including but not limited to, the methods described herein. The targeted genes of the invention include DNA sequences which are designed to specifically alter cognate endogenous alleles.

Methods of use for the transgenic mice of the invention are also provided herein. Knockout mice of the invention can be assessed for the acquisition of developmental abnormalities and various cancers, such as, for example, neuroblastoma. Knock out mice provide biological systems in which to evaluate the roles played by the 1p36.3 genes disclosed herein in such physiological processes. Accordingly, therapeutic agents which modulate the action of 1p36.3 encoded proteins (e.g., CHD5) may be screened in studies using 1p36.3 gene knock out mice.

As described above, nucleic acids encoding CHD5 protein are also used to advantage to produce large quantities of a substantially pure 1p36.3 protein, or selected portions thereof.

B. Proteins

Full-length CHD5 of the present invention may be prepared in a variety of ways, according to known methods. The protein may be purified from appropriate sources, e.g., human or animal cultured cells or tissues, by immunoaffinity purification. However, this is not a preferred method due to the small amounts of protein likely to be present in a given cell type at any time.

The availability of nucleic acid molecules encoding CHD5 provided herein enables production of the protein using in vitro expression methods known in the art. For example, a cDNA or gene may be cloned into an appropriate in vitro transcription vector, such a pSP64 or pSP65 and the like for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

Alternatively, in a preferred embodiment, larger quantities of CHD5 may be produced by expression in a suitable prokaryotic or eukaryotic system. For example, part or all of a DNA molecule, such as the cDNA having SEQ ID NO: 1, may be inserted into a plasmid vector adapted for expression in a bacterial cell, such as E. coli, or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The CHD5 produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The CHD5 proteins of the invention, prepared by the aforementioned methods, may be analyzed according to standard procedures. For example, such proteins may be subjected to amino acid sequence analysis, according to known methods.

The present invention also provides methods of use of antibodies capable of immunospecifically binding to proteins of the invention. Polyclonal antibodies directed toward CHD5 or fragments thereof may be prepared according to standard methods. In a preferred embodiment, monoclonal antibodies are prepared, which react immunospecifically with various epitopes of CHD5. In a particularly preferred embodiment, antibodies may be generated in response to amino acids 1700-1940 of CHD5. This region of CHD5 exhibits a high degree of divergence with regard to the other CHD family members and, therefore, may comprise a particularly distinctive spectrum of CHD5-specific antigenic epitopes. CHD5 also differs from its most closely related family members (i.e., CHD3 and CHD4) in other regions, including: a 34 amino acid CHD5-specific insertion following the helicase domain (residues 1334-1367) and a unique 50-residue C-terminus.

Monoclonal antibodies may also be prepared according to general methods of Köhler and Milstein, following standard protocols. Polyclonal and/or monoclonal antibodies may be prepared as described in several laboratory protocol handbooks, including: Molecular Cloning: A Laboratory Manual, Sambrook et al. eds., Cold Spring Harbor Laboratory Press (1989); Ausubel et al. (supra), and Antibodies: A Laboratory Manual, Harlow and Lane eds., Cold Spring Harbor Laboratory Press (1988).

Polyclonal or monoclonal antibodies that immunospecifically interact with CHD5 may be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of anti-CHD5 antibodies are described below.

III. Uses of CHD5-Encoding Nucleic Acids, CHD5 Proteins and Antibodies thereto

CHD5 is involved in transcriptional regulation and maintenance and regulation of chromatin structure, particularly in neural tissue and cells derived from the neural crest (Example I). In view of the above activities, CHD5 plays a role in neural development and reduction or loss of CHD5 function appears to contribute to tumorigenesis of neural-derived cells. Accordingly, the CHD5-encoding nucleic and amino acid sequences and CHD5 antibodies of the present invention may be used to advantage as a diagnostic indicator of a tumor and as a prognostic indicator for a patient with such a tumor. Such CHD5 reagents may also be useful in prenatal screening assays and diagnostic assays performed on a patient of any age suspected of having a defect or disorder of the nervous system, including cancers of the nervous system (e.g., neuroblastoma). Recombinant cells expressing the CHD5 sequences of the invention are provided herein for use in screening assays to assess agents which modulate CHD5 mediated regulation of downstream genes and chromatin structure and/or topology.

Additionally, CHD5 nucleic acids, proteins and antibodies thereto, according to this invention, may be used as research tools to identify other proteins that are intimately involved in chromatin unwinding, DNA repair and recombination, and transcriptional regulation. Biochemical elucidation of proteins which interact physically and/or biochemically with CHD5 will facilitate the identification and characterization of agents which can be used to modulate CHD5 activity.

A. Nucleic Acids Encoding CHD5

Nucleic acids encoding CHD5 may be used for a variety of purposes in accordance with the present invention. CHD5-encoding DNA, RNA, or fragments thereof may be used as probes to detect the presence of and/or expression of genes encoding CHD5. Methods in which CHD5-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR).

Nucleic acid molecules, or fragments thereof, encoding CHD5 may also be utilized to control the expression of CHD5, thereby regulating the amount of protein available to participate in chromatin organization and transcriptional regulation. Alterations in the physiological amount of CHD5 may act to modulate transcription of certain genes in cells, which may in turn alter the development and/or tumorigenic potential of such a cell. In one embodiment, the nucleic acid molecules of the invention will be used to create recombinant cell lines for use in assays to identify agents which modulate CHD5 mediated regulation of transcription and chromatin structure.

As described above, CHD5-encoding nucleic acids are also used to advantage to produce large quantities of substantially pure CHD5 protein, or selected portions thereof. The full-length protein or a selected domain can be used for research, diagnostic and therapeutic purposes, as described below.

A wide variety of expression vectors are available and can be modified to express the novel DNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology, Third Edition, 16.3-17.44 (2001). Expression methods in *Saccharomyces* are also described in Current Protocols in Molecular Biology (1989).

Suitable vectors for use in practicing the invention include prokaryotic vectors such as the pNH vectors (Stratagene Inc., 11099 N. Torrey Pines Rd., La Jolla, Calif. 92037), pET vectors (Novogen Inc., 565 Science Dr., Madison, Wis. 53711) and the pGEX vectors (Pharmacia LKB Biotechnology Inc., Piscataway, N.J. 08854). Examples of eukaryotic vectors useful in practicing the present invention include the vectors pRc/CMV, pRc/RSV, and pREP (Invitrogen, 11588 Sorrento Valley Rd., San Diego, Calif. 92121); pcDNA3.1/V5&His (Invitrogen); baculovirus vectors such as pVL1392, pVL1393, or pAC360 (Invitrogen); and yeast vectors such as YRP17, YIP5, and YEP24 (New England Biolabs, Beverly, Mass.), as well as pRS403 and pRS413 (Stratagene Inc.); Picchia vectors such as pHIL-D1 (Phillips Petroleum Co., Bartlesville, Okla. 74004); and retroviral vectors such as pLNCX and pLPCX (Clontech).

Promoters for use in expression vectors of this invention include promoters that are operable in prokaryotic or eukaryotic cells. Promoters that are operable in prokaryotic cells include lactose (lac) control elements, bacteriophage lambda (pL) control elements, arabinose control elements, tryptophan (trp) control elements, bacteriophage T7 control elements, and hybrids thereof. Promoters that are operable in eukaryotic cells include Epstein Barr virus promoters, adenovirus promoters, SV40 promoters, Rous Sarcoma Virus promoters, cytomegalovirus (CMV) promoters, baculovirus promoters such as AcMNPV polyhedrin promoter, Picchia promoters such as the alcohol oxidase promoter, and *Saccharomyces* promoters such as the gal4 inducible promoter and the PGK constitutive promoter.

In addition, a vector of this invention may contain any one of a number of various markers facilitating the selection of a transformed host cell. Such markers include genes associated with temperature sensitivity, drug resistance, or enzymes associated with phenotypic characteristics of the host organisms. Expression of such markers in cells confers upon the cells the ability to survive in the presence of a selection agent.

B. CHD5 Protein and Antibodies

After a DNA sequence encoding CHD5 or a fragment thereof has been inserted into a vector, the vector may be used to transform a host cell. In general, the host cell may comprise any cellular organism including a prokaryotic cell or eukaryotic cell that is capable of being transformed with the vector comprising the DNA of the present invention. Techniques of transforming and transfecting cells are well known in the art and may be found in such general references as Sambrook et al. (1989) or Current Protocols in Molecular Biology (1989).

The present invention is not limited to use in a particular host cell. The vectors of the invention can be transformed into and expressed in many host cells. Transformed host cells of this invention may be cultured in conventional nutrient media modified as appropriate for inducing promoters, selecting transformants or amplifying genes. The culture conditions, such as temperature, pH and the like, are those previously used with the host cell selected for expression, and will be apparent to the ordinarily skilled artisan.

The choice of a particular host cell depends to some extent on the particular expression vector used to drive expression of CHD5. After transformation of a vector of the invention into a host cell one can select transformants on the basis of a selectable phenotype. This selectable phenotype can be conferred by a selectable marker present on the expression vector.

Suitable host cells include, for example, prokaryotic cells such as *Escherichia coli* and *Bacillus subtilis*; eukaryotic cells such as Mardin Darby canine kidney (MDCK) cells (American Type Culture Collection (ATCC) CCL-34), Cos 7 cells (ATCC CRL-1651), 293 cells (ATCC CRL-1573), Chinese hamster ovary cells CHO-DHFR-(ATCC CRL-9096), Chinese hamster ovary cells CHO-K1 (ATCC CCL-61), Syrian Hamster cells AV12 (ATCC CRL 1573), human lymphocyte CCRF-CEM cells, human neuroblastoma cells, and cells derived from liver, brain, skin, and adrenal gland; yeast cells, including *Saccharomyces cerevisiae* and *Picchia pastoris*; insect cells including armyworm cells, such as *Spodoptera frugiperda* Sf9 (ATCC CRL 1711); and fungal cells including *Aspergillus* species.

Expression in prokaryotic and eukaryotic cells is described by Sambrook et al. (1989), and Kaufmann, Genetic Engineering Principles and Methods, ed. J. K. Setlow, Plenum Press 9:155, (1988). Yeast expression is described by Barr, et al., Yeast Genetic Engineering, eds. Butterworth, Boston 1989. Expression in insect cells is described by Maeda, 1989, Annual Review of Entomology 34:351.

As indicated above, the present invention provides methods for measuring CHD5 mediated chromatin remodeling, transcriptional regulation, and modulation of oncogenesis in a cellular context. Such methods are applicable to the screening of compounds to test the ability of an individual compound or combination of compounds to modulate CHD5 activity in the above assays. Thus, one embodiment of this invention provides a method for assaying CHD5 activity in a cell having the following steps: a) contacting the compound with a cell that is transformed with a recombinant DNA expression vector which provides for expression of CHD5 activity, and b) assaying for modulation of CHD5 transcription, translation, and/or activity of CHD5 in said cell.

Illustrative recombinant DNA expression vectors which provide expression of CHD5 activity that are useful in the method of this invention are described herein. Such recombinant DNA expression vectors can be tailored for optimal expression of CHD5 activity in a particular host cell.

A wide variety of cells, including those described above, may be used in this method. Cells that lack CHD5 activity before transformation with a recombinant DNA expression vector of this invention are especially useful in the method. Also useful are cells that possess measurable CHD5 activity before transformation with a recombinant DNA expression vector of this invention. In either case, cells that are transformed with a recombinant DNA expression vector encoding CHD5 activity can be assayed for CHD5 activity in the cell.

CHD5 deficient mutants of the above-referenced cells will also be useful in the method of the present invention. For example, many of the neuroblastoma cell lines screened in Example I may be considered deficient and/or null mutants for CHD5 expression. They may also be described, depending on the genotype, as hemizygous (one copy) or homozygously deleted (no copies).

As noted above, the choice of vector used to express CHD5 will vary depending on the host cell that is utilized.

Purified CHD5, or fragments thereof, may be used to produce polyclonal or monoclonal antibodies which also may serve as sensitive detection reagents for the presence and accumulation of CHD5 (or complexes containing CHD5) in cultured cells or tissues from living patients (the term "patients" refers to both humans and animals). Recombinant techniques enable expression of fusion proteins containing part or all of the CHD5 protein. The full length protein or fragments of the protein may be used to advantage to generate an array of monoclonal antibodies specific for various epitopes of the protein, thereby providing even greater sensitivity for detection of the protein in cells or tissues.

Polyclonal or monoclonal antibodies immunologically specific for CHD5 may be used in a variety of assays designed to detect and quantitate the protein, which may be useful for diagnosing a CHD5-related disease in a patient. In view of the expression pattern of CHD5, it may be implicated in disorders related to neural and adrenal development and tumorigenesis. Such assays include, but are not limited to: (1) flow cytometric analysis; (2) immunochemical localization in CHD5 in cultured cells or tissues; and (3) immunoblot analysis (e.g., dot blot, Western blot) of extracts from various cells and tissues. Additionally, as described above, anti-CHD5 can be used for purification of CHD5 (e.g., affinity column purification, immunoprecipitation).

From the foregoing discussion, it can be seen that CHD5-encoding nucleic acids and CHD5 proteins of the invention can be used to modulate CHD5 gene expression and protein activity for the purposes of assessing the impact of CHD5 modulation on organ development and tumorigenesis. In view of the tissue specific expression pattern of CHD5, evaluating the role of CHD5 in transcriptional regulation in the nervous system, neural development and tumorigenesis may be particularly useful.

Although the compositions of the invention have been described with respect to human therapeutics, it will be apparent to one skilled in the art that these tools will also be useful in animal and cultured cell experimentation with respect to chromatin structure and regulation of transcription. As therapeutics, they can be used either alone or as adjuncts to other drugs for improving the effectiveness of such agents.

IV. Kits for Performing the Disclosed Methods

Kits are also provided to facilitate the detection of CHD5 in biological samples. Exemplary approaches for detecting CHD5 nucleic acid or polypeptides/proteins include:

a) comparing sequences of nucleic acid in a sample with the wildtype CHD5 encoding nucleic acid sequence to determine whether the sample from the patient contains CHD5 sequences which are normal or altered; or b) determining the presence, in a sample from a patient, of the polypeptide encoded by the CHD5 gene and, if present, determining whether the polypeptide is full length, and/or is mutated, and/or is expressed at the normal level; or c) using DNA restriction mapping to compare the restriction pattern produced when a restriction enzyme cuts a sample of nucleic acid from the patient with the restriction pattern obtained from normal CHD5 gene or from mutations thereof; or, d) using a specific binding member capable of binding to a CHD5 nucleic acid sequence or the polypeptide encoded therefrom (either normal sequence or mutated sequence), the specific binding member may be a nucleic acid molecule hybridizable with the CHD5 sequence or an antibody with specificity for the polypeptide encoded by a native or mutated CHD5 nucleic acid sequence, the specific binding member optionally being labeled so that binding of the specific binding member to its binding partner is detectable; or, e) using PCR involving one or more primers based on normal or mutated CHD5 gene sequence to screen for normal or mutant CHD5 gene in a sample from a patient.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples and they do not need to be listed here. Further, the term "specific binding pair" is also applicable where either or both of the specific binding member and the binding partner comprise a part of a large molecule. In embodiments in which the specific binding pair are nucleic acid sequences, they will be of a length to hybridize to each other under conditions of the assay, preferably greater than 10 nucleotides long, more preferably greater than 15 or 20 nucleotides long.

In most embodiments for screening for cancer susceptibility alleles, the CHD5 nucleic acid in the sample will initially be amplified, e.g. using PCR, to increase the amount of the analyte as compared to other sequences present in the sample. This allows the target sequences to be detected with a high degree of sensitivity if they are present in the sample. This initial step may be avoided by using highly sensitive array techniques that are becoming increasingly important in the art.

The identification of the CHD5 gene and its potential association with cancer paves the way for aspects of the present invention to provide the use of materials and methods, such as are disclosed and discussed above, for establishing the presence or absence in a test sample of a variant form of the gene, in particular an allele or variant specifically associated with cancer, especially neuroblastoma. This may be useful for diagnosing a predisposition of an individual to cancer or for diagnosing the type of cancer presented by a patient as being associated with the gene.

In still further embodiments, the present invention concerns immunodetection methods for binding, purifying, removing, quantifying or otherwise generally detecting biological components. In general, the immunobinding methods include obtaining a sample suspected of containing a protein or peptide, and contacting the sample with an antibody in accordance with the present invention, as the case may be, under conditions effective to allow the formation of immunocomplexes.

The immunobinding methods include methods for detecting or quantifying the amount of a reactive component in a sample, which methods require the detection or quantitation of any immune complexes formed during the binding process. Here, one would obtain a sample suspected of containing a CHD5 gene encoded protein or peptide, and contact the sample with an antibody and then detect or quantify the amount of immune complexes formed under the specific conditions.

In terms of antigen detection, the biological sample analyzed may be any sample that is suspected of containing altered amounts of the CHD5 antigen, such as a tumor (e.g., neuroblastoma) tissue section or specimen, a homogenized tissue extract, an isolated cell, a cell membrane preparation, separated or purified forms of any of the above protein-containing compositions, or even any biological fluid that comes into contact with neuroblastoma tissues, including blood, lymphatic, and cerebrospinal fluid.

Contacting the chosen biological sample with an antibody under conditions effective and for a period of time sufficient to allow the formation of immune complexes (primary immune complexes) is generally a matter of simply adding the composition to the sample and incubating the mixture for a period of time long enough for the antibodies to form immune complexes with, i.e., to bind to, any antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary-binding ligand such as a second antibody or a biotin/avidin ligand binding arrangement, as is known in the art.

The immunodetection methods of the present invention have evident utility in the diagnosis of neuroblastoma. Here, a biological or clinical sample suspected of containing altered levels of either the encoded protein or peptide is used.

In the clinical diagnosis or monitoring of patients with neuroblastoma, the detection of CHD5, or a decrease in the levels of such an antigen, in comparison to the levels in a corresponding biological sample from a normal subject is indicative of a patient with neuroblastoma. The basis for such diagnostic methods lies, in part, with the finding that the CHD5 nucleic acid identified in the present invention is not detectable or minimally expressed in neuroblastoma cell lines (see Example I below). By extension, it may be inferred that decreased levels of CHD5 nucleic acid or protein expression may also be used as markers of neuroblastoma.

In one broad aspect, the present invention encompasses kits for use in detecting expression of CHD5 in tumor biopsy samples. Such a kit may comprise one or more pairs of primers for amplifying nucleic acids corresponding to the CHD5 gene. The kit may also comprise buffers, nucleotide bases, and other compositions to be used in hybridization and/or amplification reactions. Each solution or composition may be contained in a vial or bottle and all vials held in close confinement in a box for commercial sale.

Another embodiment of the present invention encompasses a kit for use in detecting CHD5 antigen in tumor biopsy samples. Such a kit may comprise antibodies or antibody fragments immunologically specific for CHD5 and means for assessing the formation of immunocomplexes containing CHD5.

V. Therapeutics

A. Rational Drug Design

Since CHD5 is a member of the chromodomain family, a family of proteins which plays a role in the maintenance of appropriate chromatin structure and transcriptional regulation, methods for identifying agents that modulate its activity are highly desirable. Such agents should have utility for the treatment of a variety of diseases The CHD5 polypeptide or fragment employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between a CHD5 polypeptide or fragment and the agent being tested, or examine the degree to which the formation of a complex between a CHD5 polypeptide or fragment and a known compound is interfered with by the agent being tested.

Another technique for drug screening provides high throughput screening for compounds having suitable binding affinity to CHD5 polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with CHD5 polypeptide and washed. Bound CHD5 polypeptide is then detected by methods well known in the art.

A further technique for drug screening involves the use of host eukaryotic cell lines or cells (such as described above) which have a nonfunctional CHD5 gene. These host cell lines or cells are defective at the CHD5 polypeptide level. The host cell lines or cells are grown in the presence of a drug compound to determine if the compound is capable of regulating and/or restoring chromatin structure and gene transcription in CHD5 defective cells.

Another approach entails the use of phage display libraries engineered to express fragments of CHD5 on the phage surface. Such libraries are then contacted with a combinatorial chemical library under conditions wherein binding affinity between the CHD5 peptides and the components of the chemical library may be detected. U.S. Pat. Nos. 6,057,098 and 5,965,456 provide methods and apparatus for performing such assays.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, discussed above, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides (e.g., CHD5 polypeptide) may be analyzed by an alanine scan (Wells, (1991) Meth. Enzym. 202:390-411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based.

It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-ids could then be used to identify and isolate peptides from banks of chemically or biologically produced peptides. Selected peptides would then act as the pharmacore.

Thus, it is clear from the foregoing that one may design drugs which have, e.g., improved CHD5 polypeptide activity or stability or which act as inhibitors, agonists, antagonists, etc. of CHD5 polypeptide activity. By virtue of the identification of a full length CHD5 clone as described herein, sufficient amounts of the CHD5 polypeptide may be made available to perform such analytical studies as x-ray crystallography. In addition, the knowledge of the CHD5 protein sequence provided herein will guide those employing computer modeling techniques in place of, or in addition to x-ray crystallography.

Suitable peptide targets for identifying specific CHD5 binding and modulating agents include, but are not limited to: PHD zinc fingers (amino acids 345-390 and 418-463); chromodomains (amino acids 510-525 and 596-625); the DEAH-box-type helicase domain (amino acids 703-999); and the SNF2 domain (amino acids 1054-1138).

B. Pharmaceuticals and Peptide Therapies

The identification of a full length CHD5 clone as described herein facilitates the development of pharmaceutical compositions useful for the development of optimal drugs for the treatment of patients with a variety of diseases, including neuroblastoma. Utilizing methods of the present invention, such CHD5 activity-modulating drugs can be optimized for both the timing of delivery and maximal uptake in, for example, cells of the adrenal gland and nervous system and tumor cells (e.g., neuroblastoma cells). These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

The following Examples are provided to describe the invention in further detail. The Examples are intended to illustrate and not to limit the invention.

EXAMPLES

Example I

Cloning and Characterization of Full Length CHD5

The following methods are provided to facilitate the practice of Example I.

Materials and Methods

DNA-based Bioinformatics. Draft genomic sequence from P1-artificial (PAC) clones RP11-461L11 and RP11-233K16 (GenBank accession numbers AC026968 and AL035406, respectively) were analyzed with the ab initio gene prediction program Genscan (genes.mit.edu/GENSCAN.html) and the sequence annotation resource Ensembl www.ensembl.org to identify putative coding regions. Predicted exon sequences were then used to search GenBank using BLAST (www.ncbi.nlm.nih.gov/BLAST) to identify homologies and similarities to known genes and proteins. Exon/intron boundaries were determined by an alignment of the full-length CHD5 cDNA sequence with the corresponding genomic sequence (GenBank accession NT_019265) using BLAST 2 sequences (8). For evaluation of Genscan and Ensembl, exon sensitivity, exon specificity, whole exon, and missing exon rates were calculated and defined as described by Reese (9).

EST and genomic DNA alignments were performed using the genomic analysis software package MacVector version 6.5.3. (Accelrys, San Diego, Calif.). EST and SAGE data were obtained from the National Center for Biotechnology Information at www.ncbi.nlm.nih.gov/SAGE/ and www.ncbi.nlm.nih.gov/UniGene, respectively. CpG island identification was performed with the algorithm CPG (www.emboss.org/). Promoter analysis was performed using TESS at the Baylor College of Medicine (searchlauncher.bcm.tmc.edu/)

Protein-based Bioinformatics. Protein motifs were identified by queries of the Pfam protein domain database (www.sanger.ac.uk/Software/Pfam/), Interpro (www.ebi.ac.uk/interpro/), BLASTP, and visual inspection of sequence alignments with additional CHD family members. Alignment of protein sequences for HsCHD1 (Homo sapiens CHD1), HsCHD2, HsCHD3, HsCHD4, HsCHD5, dMi-2 (*Drosophila*), and a predicted MmCHD5 (Mus musculus CHD5) was performed using the Clustal W algorithm in MacVector. GenBank accession numbers of the identified proteins are as follows: HsCHD1 (XP-004000), HsCHD2 (XP-007722), HsCHD3 (NP-001263), HsCHD4 (NP-001264), and dMi-2 (AAD17276) The prediction of the possible mouse ortholog of the human CHD5 was performed by database searches at the NCBI using TBLASTN and BLASTN against mouse ESTs. Although a large number of homologous ESTs were likely to be the orthologs of other CHD gene family members according to the predicted protein sequences, one clone (GenBank: AK015949) was completely homologous within stretches of HsCHD5 alone.

Cell Lines and Nucleic Acid Isolation. Cell line specifics, culture conditions, and DNA extraction methods for neuroblastoma cell lines CHLA-51, CHLA-79, CHLA-90, CHLA-123, CHLA-150, CHP-134, CHP-901, CHP-902R, IMR-5, KCN, KCN-R, LA-N-5, NB69, NBLS, NGP, NLF, NMB, OAN, SK-N-AS, SK-N-BE(2), SK-N-DZ, SK-N-FI, SK-N-SH, and SMS-KAN were performed as previously described (10). Total mRNA was isolated from cell lines using the Totally RNA® system (Ambion, Austin, Tex.), and a panel of 15 normal tissue mRNAs was purchased from Clontech (Clontech Labs, Palo Alto, Calif.). cDNA was generated using a Superscript II RT® Kit (Invitrogen, Carlsbad, Calif.). Poly $A^+$ RNA was extracted from cell line RNAs using the Oligotex poly $A^+$ purification kit (Qiagen, Valencia, Calif.).

DNA Sequencing, Northern Analysis, and 5' RACE. DNA sequences for CHD5 were obtained on an Applied Biosystems Model 3700 DNA sequencer using the ABI PRISM® BigDye™ Primer Cycle Sequencing Kit (Applied Biosystems, Foster City, Calif.) (11). The 5' end of CHD5 was obtained by sequencing of a PCR fragment amplified using the 5' RACE System, Version 2.0 (Invitrogen, Carlsbad, Calif.). Primer sequences used for 5' RACE were 5'-TCATCATTGCTCCCCTCTTT (SEQ ID NO: 3) for the initial amplification and 5'-TTCTTCCGCTTCCCTTTACA (SEQ ID NO: 4) for the second round of amplification.

Real-Time RT-PCR (TaqMan). Gene-specific primers and fluorescent probes were identified using Primer Express 5.1 and obtained from Applied Biosystems (www.appliedbiosystems.com/updates/oligos.html). CHD5 amplification primer sequences used were 5'-CCGAGATCCCAAACGGTG (SEQ ID NO: 5) and 5'-CCAGTGTAGAATCCGCTGGAC (SEQ ID NO: 6); the oligonucleotide sequence used for amplification product detection was 5'-CTCTGCCCGCGCTGTACTTGCC (SEQ ID NO: 7). Primers and probes for glyceraldehyde-3-phosphate dehydrogenase (GAPDH), a ubiquitously expressed housekeeping gene multiplexed along with the candidate gene to provide an internal control and for quantification, were purchased from Applied Biosystems. Each amplification reaction contained 1X Master Mix (Applied Biosystems), 50 ng of cDNA, 5 μM GAPDH detection primer, 5 μM CHD5 detection primer, 10 μM of each GAPDH amplification primer, and 10 μM of each CHD5 amplification primer. Samples were amplified in triplicate in 20 μl reaction volumes in a 96-well format, using conditions of one cycle at 50° C. for 2 minutes; 1 cycle at 95° C. for 10 minutes; 55 cycles at 95° C. for 15 seconds and then 60° C. for 1 minute. Standards with known DNA concentrations were included in every run for reaction controls. Assays were performed on an ABI Prism 7700 Sequence detection system. Signals were normalized and quantified relative to GAPDH with the associated program Sequence Detector v1.7, using the comparative method.

Results

Identification of CHD5 within 1p36.3. It had been previously established that PACs RPCI-11-120G22 and RPCI-11-233K16 lie within a region of 1p36.3, which is consistently deleted in primary human neuroblastomas (5, 12). The complete DNA sequence of these two clones was subsequently determined in cooperation with the Sanger Institute (12, 13), and the sequences were shown to partially overlap. Gene prediction algorithm analysis of this sequence contig predicted a large, multiexonic gene spanning portions of both cloned sequences. The 3' half of the predicted gene sequence demonstrated nearly perfect homology to the entire reported sequence of two partial cDNAs (KIAA0444/AB007913 and DKEZp434N231/AL117491) in Genbank. In addition, the 3' end of the predicted gene sequence matched the consensus sequence of a cluster of 60 expressed sequence tags (ESTs) (Unigene EST cluster Hs.158291; www.ncbi.nlm.nih.gov/UniGene), strongly suggesting that this was an authentic transcript. The UniGene cluster record indicated strong paralogy to members of the CHD family of chromatin structure regulators. Accordingly, the gene was designated CHD5. Homologous cDNA sequences in mouse, rat, and chicken, as well as *X. laevus, Arabidopsis, C. elegans, D. melanogaster, S. cerevisiae, S. pombe,* and *P. falciparum* were also identified, indicating that this gene or its parent gene family is highly conserved in eukaryotes.

TABLE III

Genomic Structure of Human CHD5

| Exon Number | Exon Start (bp) | Exon End (bp) | Exon Size (bp) | Exon/Intron Interface | Intron Number | Intron Size (bp) |
|---|---|---|---|---|---|---|
| 1 | 1 | 179 | 179 | gt/ag | 1 | 11667 |
| 2 | 180 | 307 | 128 | gt/ag | 2 | 8634 |
| 3 | 308 | 487 | 180 | gt/ag | 3 | 3618 |
| 4 | 488 | 606 | 119 | gt/ag | 4 | 700 |
| 5 | 607 | 845 | 239 | gt/ag | 5 | 2123 |
| 6 | 846 | 970 | 125 | gt/ag | 6 | 1256 |
| 7 | 971 | 1094 | 124 | gt/ag | 7 | 1619 |
| 8 | 1095 | 1261 | 167 | gt/ag | 8 | 170 |
| 9 | 1262 | 1483 | 222 | gt/ag | 9 | 1982 |
| 10 | 1484 | 1690 | 207 | gt/ag | 10 | 241 |
| 11 | 1691 | 1902 | 212 | gt/ag | 11 | 2056 |
| 12 | 1903 | 2034 | 132 | gt/ag | 12 | 92 |
| 13 | 2035 | 2143 | 109 | gt/ag | 13 | 1217 |
| 14 | 2144 | 2335 | 192 | gt/ag | 14 | 85 |
| 15 | 2336 | 2536 | 201 | gt/ag | 15 | 5262 |
| 16 | 2537 | 2674 | 138 | gt/ag | 16 | 89 |
| 17 | 2675 | 2796 | 122 | gt/ag | 17 | 1113 |
| 18 | 2797 | 2970 | 174 | gt/ag | 18 | 370 |
| 19 | 2971 | 3112 | 142 | gt/ag | 19 | 458 |
| 20 | 3113 | 3244 | 132 | gt/ag | 20 | 2379 |
| 21 | 3245 | 3362 | 118 | gt/ag | 21 | 1302 |
| 22 | 3363 | 3487 | 125 | gt/ag | 22 | 1134 |
| 23 | 3488 | 3719 | 232 | gt/ag | 23 | 228 |
| 24 | 3720 | 3830 | 111 | gt/ag | 24 | 280 |
| 25 | 3831 | 4003 | 173 | gt/ag | 25 | 1299 |
| 26 | 4004 | 4178 | 175 | gt/ag | 26 | 713 |
| 27 | 4179 | 4271 | 93 | gt/ag | 27 | 153 |
| 28 | 4272 | 4360 | 89 | gt/ag | 28 | 228 |
| 29 | 4361 | 4494 | 134 | gt/ag | 29 | 438 |
| 30 | 4495 | 4639 | 145 | gt/ag | 30 | 408 |
| 31 | 4640 | 4799 | 160 | gt/ag | 31 | 2374 |
| 32 | 4800 | 4879 | 80 | gt/ag | 32 | 256 |
| 33 | 4880 | 5012 | 133 | gt/ag | 33 | 8106 |
| 34 | 5013 | 5102 | 90 | gt/ag | 34 | 581 |
| 35 | 5103 | 5240 | 138 | gt/ag | 35 | 256 |
| 36 | 5241 | 5349 | 109 | gt/ag | 36 | 1248 |
| 37 | 5350 | 5482 | 133 | gt/ag | 37 | 403 |
| 38 | 5483 | 5678 | 196 | gt/ag | 38 | 3015 |
| 39 | 5679 | 5842 | 164 | gt/ag | 39 | 106 |
| 40 | 5843 | 5957 | 115 | gt/ag | 40 | 107 |
| 41 | 5958 | 6011 | 54 | gt/ag | 41 | 806 |
| 42 | 6012 | 9646 | 3635 | | | |
| Total | | | 9646 | | | 68572 |

CHD5 Genomic Structure. CHD5 is comprised of 42 exons spanning 78,218 bp of genomic distance (Table II). The exon lengths range from 54 (exon 41) to 3,635 bp (exon 42), with the largest exon entirely within the coding region being 239 bp (exon 5). The putative initiating AUG was within exon 1. The last exon contained the entire 3' UTR, as is commonly observed for mammalian genomic structures. The introns ranged in size from 85 bp (intron 5) to 11,667 bp (intron 1). The two PHD domains spanned portions of exons 8-9 and 9-10, while the two chromodomains were contained within exons 10 and 11-12. The SNF2 and helicase domains spanned exons 14-19 and 21-23, respectively. Interestingly, all six domain structures were confined to only a central 16 of the 41 exons. Strong homology to other CHD family members outside of the identified domains suggested the presence of additional functional elements elsewhere in the protein (data not shown). No evidence was found for transcripts contained within any of the CHD5 introns, although the possible presence of additional functional open reading frames cannot be ruled out.

CHD5 was physically juxtaposed between two previously characterized genes. The ribosomal protein RPL22 was aligned with CHD5 in a tail-to-head configuration, with 6.4 kb separating the 3' end of RPL22 and the transcriptional start site of CHD5. The 3' end of CHD5 was aligned tail-to-tail with the potassium channel KCNAB2, with the two transcriptional ends separated by 1.3 kb. This configuration rendered it unlikely that CHD5 shared transcriptional regulation with its nearest neighbors. A 200-kb window encompassing CHD5 had a GC content of 55.2%, indicating that CHD5 was likely to be within a gene-rich region. Analysis of the CHD5 genomic sequence revealed the presence of a CpG island commencing 630 bp 5' of the transcriptional start and containing all of exon 1 as well as the initial 680 bp of intron 1.

Because of known limitations by gene prediction algorithms in identifying genomic structures of large genes, the experimentally determined genomic structure was compared with the predictions from Genscan and Ensembl. Three evaluations were used: exon sensitivity (% of exons identified at least in part), exon specificity (% of exons predicted that are true exons), and exon identity (% of actual exons that were perfectly predicted positionally). Genscan had a sensitivity of 98%, a specificity of 93%, and an exon identity of 81%, while Ensembl had a sensitivity of 84%, a specificity of 100%, and an exon identity of 74%.

CHD5 mRNA Analysis. The predicted CHD5 sequence extended for 3.0 and 1.8 kb 5' of the reported partial cDNA sequences of AB007913 and AL117491, respectively. RT-PCR of fetal brain mRNA using a series of primers from predicted exons that were increasingly 5' to the reported cDNAs resulted in recovery of the entire 5' coding region. The 5' untranslated region (5' UTR) and 5' mRNA transcriptional start were identified by 5' RACE (data not shown). Using primers from the 5' and 3' UTR sequences, a full-length cDNA sequence of 9.6 kb was generated from fetal brain cDNA. No evidence for alternative splicing has been observed either in RT-PCR amplification of various portions of the gene from RNA derived from multiple tissues, or in alignment of EST sequences with the consensus gene sequence.

The CHD5 cDNA sequence spanned 9,646 bp, with a 5' UTR of 100 bp, a single open reading frame of 5,865 bp, and a 3' UTR of 3,681 bp (SEQ ID NO: 1). The transcribed sequence has a GC content of 60.1%, and several local stretches (especially the 5'-most portion) exceeded 80% in GC content. A number of consensus transcription factor binding sites, including several Sp1, GCF, and AP-family sites, were present just upstream of and within the 5' UTR, although the functional significance of these sites remains to be determined. The initiator AUG has been designated at mRNA base position 101 and was preceded by an in-frame stop codon at bp 38. A consensus polyadenylation signal (AATAAA) was present 14 base pairs before the transcriptional 3' terminus. No known repetitive elements were present in the 3' UTR or elsewhere in the transcribed sequence, although the surrounding genomic region was both LINE and SINE-rich.

CHD5 Protein Analysis. Analysis of the nucleic acid sequence was performed to ascertain the CHD5 protein sequence based on the cDNA open reading frame. A protein of 1954 residues was predicted from the CHD5 open reading frame (SEQ ID NO: 2). The N-terminal portion of CHD5 was predicted to contain two zinc fingers of the PHD class (amino acid positions 345-390 and 418-463), followed closely by two chromodomains (amino acid positions 510-525 and 596-625). PHD zinc finger motifs are thought to play roles in chromatin-associated transcriptional regulation, while chromodomains are frequently observed in proteins involved in recruitment of transcriptional regulatory complexes. The central portion of the protein included a predicted DEAH-box-type helicase domain (amino acid positions 703-999) and a putative SNF2 domain (amino acid positions 1054-1138). DEAH ATP helicases are ATP-dependent and are usually associated with nucleic acid unwinding. SNF2 domains are commonly observed in, although not restricted to, proteins involved in chromatin unwinding, DNA repair and recombination, and transcriptional regulation. Several potential nuclear localization signals are also present (amino acid positions 50-67, 54-71, 97-114, 100-117, 240-257, 253-270, 918-935).

Sequence Comparison to other CHD Family Members. The extent of amino acid identity and similarity between HsCHD5 and other CHD proteins over the entire protein sequences were determined to be the following: HsCHD1, 25.4% identity (38.6% similarity); HsCHD2, 27.1% identity (41.0% similarity); HsCHD3, 70.0% identity (80.2% similarity); HsCHD4, 75.5% identity (84.4% similarity). In addition, HsCHD5 was strikingly homologous to its ortholog in *Drosophila*, dMi-2 (55.0% identity, 67.8% similarity). Moreover, sequences homologous to CHD5 have been found in a number of other metazoans (data not shown), whereas the SNF2 and helicase regions of CHD5 exhibited considerable homology to a number of proteins from bacterial and archael species.

Although all the genes that comprise the CHD family share homology in the conserved functional domains (chromodomain, DNA helicase/ATPase domain and DNA binding domain), HsCHD5 has stronger homology with HsCHD3, HsCHD4 and dMi-2 than with HsCHD1 and HsCHD2. As shown in FIG. 1, the main structural/functional difference between the CHD3/4/5 class (which includes dMi-2) and the CHD1/2 class was that only the former possessed PHD zinc finger domains. HsCHD5 shared the same number and order of functional domains with the other CHD3/4/5 class members. Moreover, long blocks of ~90% CHD3/4/5 class-specific homology outside of the characterized functional domains (residues 174-203, 1254-1327, 1403-1422, 1431-1492, 1541-1647, 1887-1910, 1919-1946, 1963-1997, and 2015-2066) were striking, indicating the likelihood of additional functional motifs. The majority of these putative motifs showed homology only to characterized CHD family proteins. CHD5 significantly diverged from both CHD3 and CHD4 only in a few regions: a 34 amino acid CHD5-specific insertion following the helicase domain (residues 1334-1367), a region of divergence stretching approximately 170 amino acids (residues 1668-1886), and a unique 50-residue C-terminus. Because other members of this class are known to be components of the NuRD complex (15, 16), it is likely that CHD5 may also participate in the formation of a functional NuRD complex. The predicted mouse ortholog (MmCHD5) has a high degree of protein sequence homology with HsCHD5 (93.0% identity, 96.0% similarity) which extends beyond the functional domains.

Figure 2A:
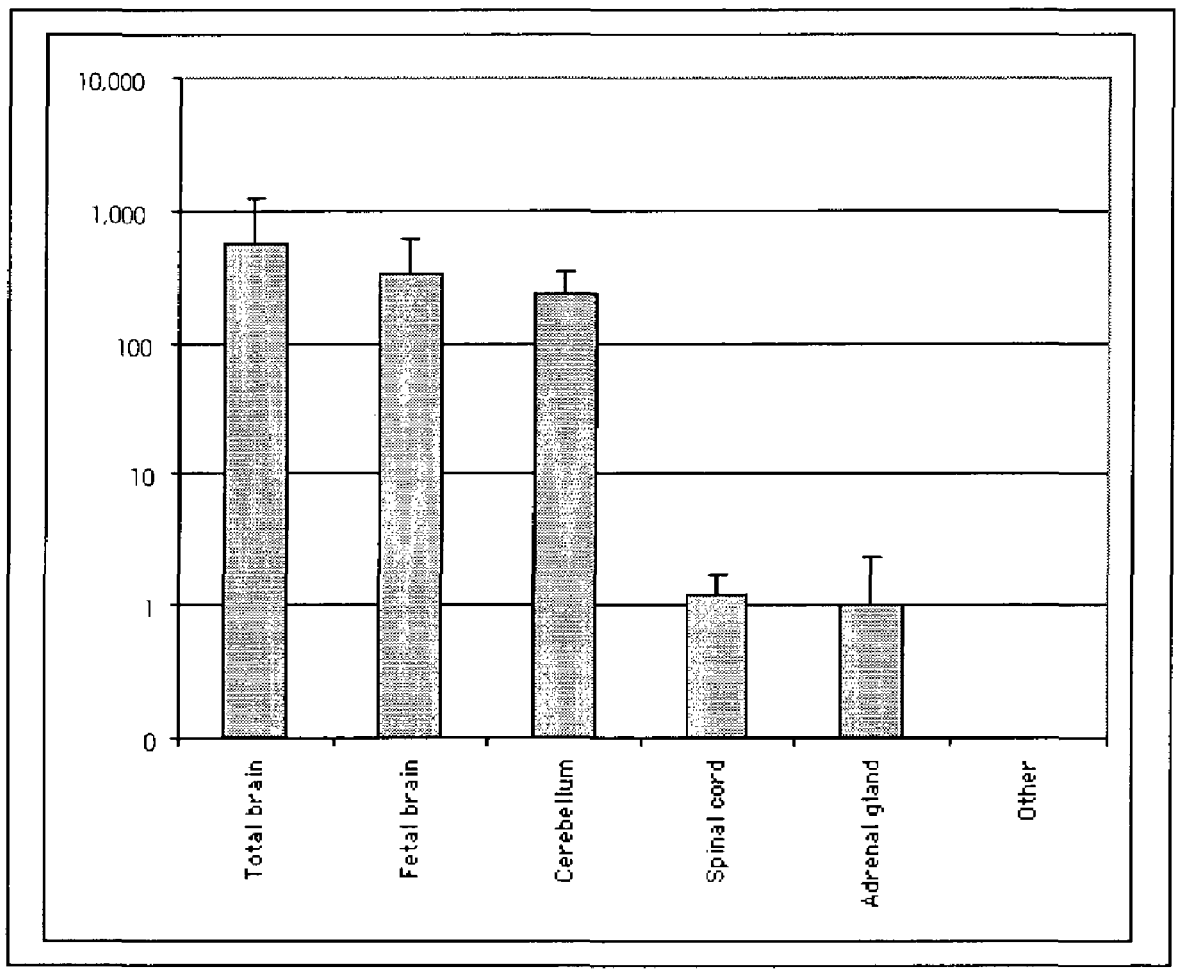
FIG. 2A is a graph showing the tissue specific expression pattern of CHD5 mRNA, as measured by quantitative real-time PCR, in a panel of normal human tissues. Expression values were normalized to GAPDH mRNA expression levels. Y-axis expression units were arbitrary. Each experiment was performed in triplicate, with error bars indicating variance. Expression was below the level of detection in most tissues. The column and far right labeled "Others" represents thirteen tissues for which no expression was detected (see text for tissue list).

Tissue Expression Profile. The cDNA libraries of over 90% of the CHD5-associated ESTs were derived from either brain or neural-derived tissues, with pancreas and testis comprising the remainder. Accessible serial analysis of gene expression (SAGE) data at the NCBI confirmed the neural-specific expression pattern, and revealed low level expression of the gene in solid tumors of the colon, prostate, pancreas, and a variety of other tissues. To determine more precisely the expression profile of CHD5, real-time quantitative PCR was performed on a panel of 18 normal tissue RNAs using a pair of CHD5 cDNA-specific primers. Detectable expression of CHD5 was limited to neural-derived tissues (fetal brain, total brain, cerebellum) and adrenal gland (FIG. 2A). CHD5 expression was not detected in the other tissues tested, including: placenta, liver, fetal liver, spleen, bone marrow, thyroid, thymus, salivary gland, stomach, pancreas, small intestine, colon, or prostate. Comparable results were obtained independently using a semi-quantitative, gel-based RT-PCR assay for CHD5 (data not shown). Interestingly, the adrenal gland is a common site for the origin of neuroblastomas (see below).

Figure 2B:
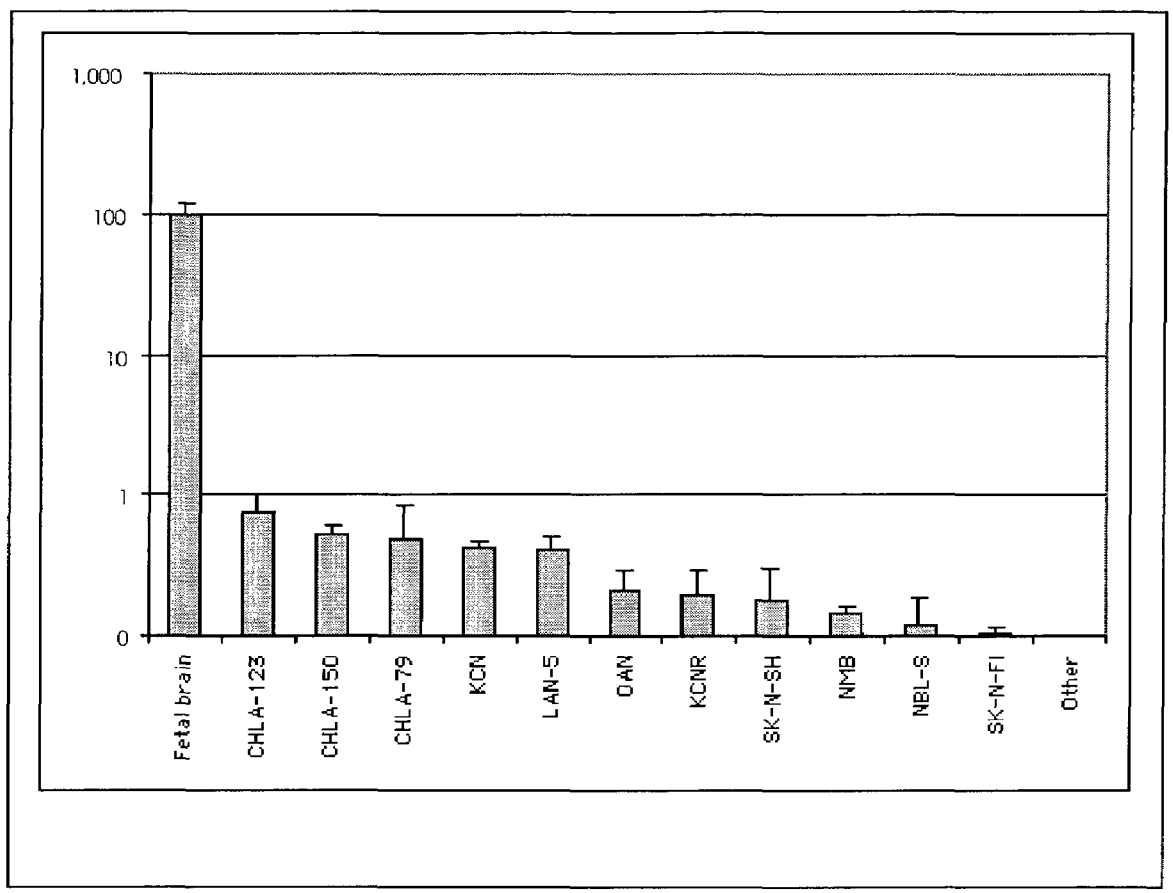
FIG. 2B is a graph showing the expression levels of CHD5 mRNA in neuroblastoma cell lines, as measured by quantitative real-time PCR, in a panel of 24 neuroblastoma cell lines and normal fetal brain. Expression values were normalized to GAPDH mRNA expression levels. Y-axis expression units were arbitrary. Each experiment was performed in triplicate, with error bars indicating variance. The column and far right labeled "Others" represents thirteen cell lines for which no expression was detected (see text for cell line list).

Expression in Neuroblastoma Cell Lines. Expression of CHD5 was also analyzed in a panel of 24 neuroblastoma cell lines by real-time PCR. A fetal brain sample was included for comparison with normal tissue expression. These cell lines were either negative for CHD5 transcript or exhibited dramatically lower levels of gene expression relative to that of fetal brain (FIG. 2B).

Specifically, thirteen cell lines (CHLA-51, CHLA-90, CHP-134, CHP-901, CHP-902R, IMR-5, NB69, NGP, NLF, SK-N-AS, SK-N-BE2, SK-N-DZ, and SMS-KAN) had no evidence of CHD5 expression, while CHD5 levels for the remaining eleven cell lines (CHLA-123, CHLA-150, CHLA-79, KCN, LAN-5, OAN, KCNR, SK-N-SH, NMB, NBL-S, and SK-N-FI) were all very low, two orders of magnitude below the level observed for normal fetal brain. Northern analysis of a subset of the neuroblastoma cell lines used in the quantitative PCR studies shown herein was in agreement with the PCR results (data not shown).

Figure 3:
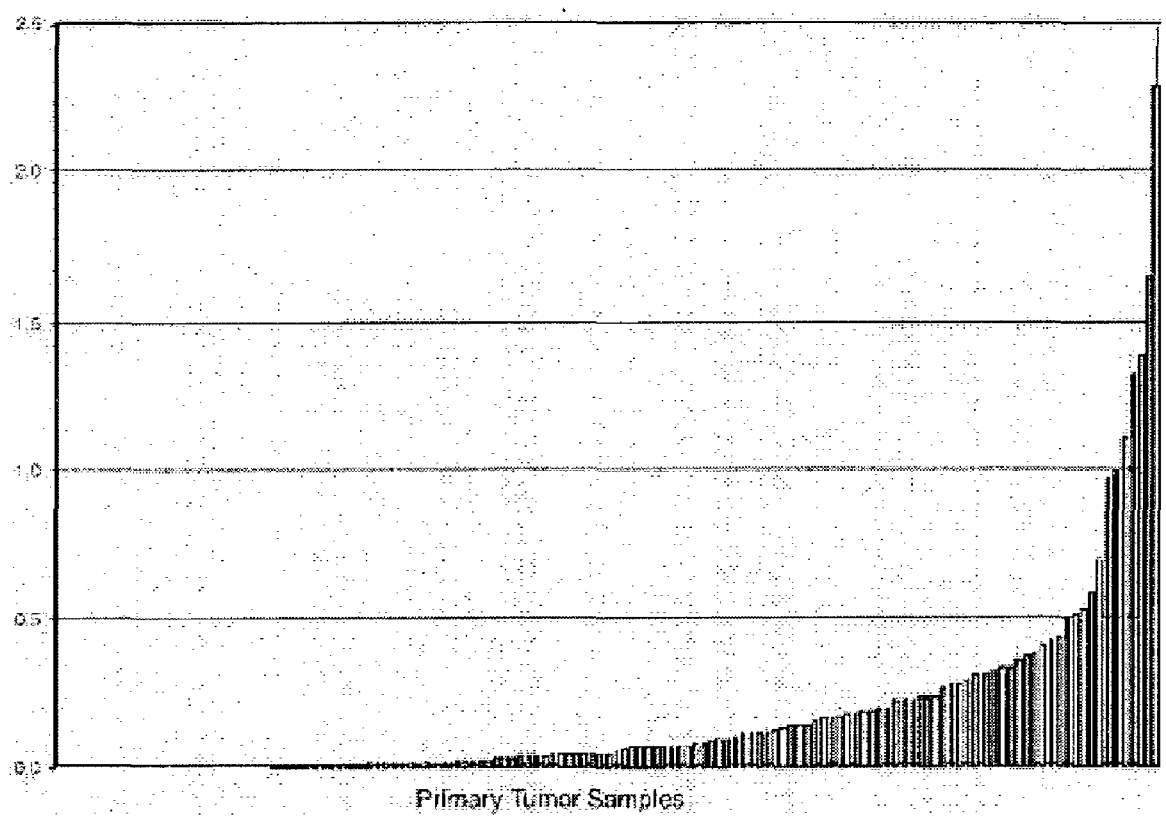
FIG. 3 is a graph showing the expression levels of CHD5 mRNA in 137 primary neuroblastomsa. Shown is the level of CHD5 mRNA expression, as measured by quantitative real-time PCR, in a panel of 137 representative primary neuroblastomas compared to normal fetal brain. Expression values are normalized to mRNA GAPDH expression levels, and all values are normalized to the expression in fetal brain (1.0 expression units on the Y-axis). Each experiment was performed in duplicate.

Expression in Primary Neuroblastomas. Finally, we examined the expression of CHD5 in a representative panel of 137 primary neuroblastomas using real-time RT-PCR (FIG. 3). Low expression was strongly correlated with 1p loss (P=0.001), MYCN amplification (P<0.001), advanced clinical stage (P=0.001), and unfavorable histology (P=0.02), but not with older age (P=0.3). Since all of these features are associated with a worse outcome, these finding demonstrate that low CHD5 expression may contribute to the unfavorable outcome seen in patients with these high risk features. We examined the gene for mutations using simple sequence conformation polymorphism (SSCP) analysis, with sequence confirmation, and only a single missense mutation was identified, revealing that while mutations can occur, this is not a common mechanism of CHD5 inactivation.

Discussion

In the process of characterizing genes that map to a region of frequent deletion on 1p36.3 in neuroblastomas, a CHD5 gene was identified herein, which encodes a protein with homology to previously identified chromodomain proteins. Other chromodomain protein family members include CHD1, which was identified in 1993 as a mammalian DNA binding protein that contained a chromodomain and a SNF2/ SWI2-like helicase domain (17). CHD2 was identified based on its homology to CHD1, but a unique role for this protein has not been identified (3). CHD3 and CHD4 were first identified as autoantigens in patients with dermatomyositis (18-20) and were subsequently found to be members of the CHD gene family. These two proteins are critical to the function of multiprotein chromatin remodeling complexes.

There are two major histone deacetylase complexes in mammalian cells. One is called NuRD (16) and the other is called Sin3 or SAP (for Sin3 Associated Protein) complex (21). Both of these complexes share four proteins-two histone deacetylases (HDAC1 and HDAC2) and two Rb-associated histone-binding proteins (RbAp46 and RbAp48). The defining protein of the NuRD complexes is a chromodomain protein of the CHD family (CHD3 or CHD4). In addition, NuRD complexes are consistently associated with at least two other proteins, called metastasis-associated protein 1 (MTA1, or MTA2) and methyl DNA binding domain protein 3 (MBD3) (21). The other major type of HDAC complex is defined by the presence of Sin3A or B proteins, which may serve as a scaffold for other proteins. The SAP complex contains at least two other unique proteins, known as SAP18 and SAP30 (21). Although the function of these proteins is not yet defined, SAP30 may facilitate the association of SAP complexes with other proteins such as transcription factors. These complexes are involved in chromatin remodeling, and they most likely cause transcriptional repression.

All of the CHD proteins have two chromodomains located in the N-terminal one-third of the protein. There is also a large SWI/SNF like helicase/ATPase domain in the central one-third of the protein. Swi/Snf proteins were initially identified in yeast as playing a role in mating type switching or sucrose metabolism, but they were subsequently found to have roles in chromatin remodeling. The CHD proteins also have a DNA binding region at the C-terminus of the protein. CHD1 and CHD2 comprise one subgroup of closely related proteins, whereas CHD3, CHD4 and CHD5 comprise a second related subgroup of CHD family proteins. The latter subgroup is distinguished from the former by the presence of two PHD domains found N-terminal to the chromodomains. Overall, the predicted homology of human CHD5 with other family members was 38.6% similarity with CHD1, 41.0% with CHD2, 80.2% with CHD3 and 84.4% with CHD4. Based on its homology to CHD3 and CHD4, CHD5 likely functions as part of a NuRD histone deacetylase complex. The CHD5 protein sequence was virtually identical to the partial sequence available for mouse CHD5 (93% identity, 96% similarity). Surprisingly, human CHD5 has 67.8% similarity to dMi-2, showing striking conservation of this protein over considerable evolutionary distance (see below).

Chromodomain proteins can affect gene expression in a developmentally restricted and gene-specific manner. The CHD protein complexes likely confer the specificity of their transcriptional repression through the recruitment of other effector proteins with which they interact. These proteins may then bind to the promoters of other genes and target histone deacetylation and transcriptional repression to these genes or chromatin regions. For example, Polycomb group (PcG) proteins maintain repression of HOX genes during development in *Drosophila*, and this transcriptional repression is site-specific (22, 23). Hunchback (Hb) also binds directly to HOX regulatory sequences and represses transcription. Interestingly, the transcriptional repression imposed by both PcG and Hb is mediated by the binding of dMi-2, a CHD homolog (22). Furthermore, during embryonic CNS development in *Drosophila*, the sequential expression in neuroblasts of four proteins, including Hb, identifies a transcription factor network regulating the temporal development of all ganglia (23).

This is a clear example of a chromodomain protein controlling the regulation of a small number of genes important in neural development.

As described herein, the expression pattern of CHD5 was examined in a variety of tissues by a quantitative real-time RT-PCR technique. CHD5 expression was higher in brain than in most other tissues by at least one to two orders of magnitude. Analysis of neural tissues in detail revealed that the highest levels of CHD5 were found in the cerebellum, followed by total brain and fetal brain, spinal cord and adrenal gland. This preferential expression in the brain and in neural tissues suggests that CHD5 may play an important role in the development of the nervous system.

A microdeletion syndrome involving 1p36.3 has been characterized which leads to a variety of congenital and developmental anomalies (24). Many of the deletions of this syndrome are localized to the region which encodes CHD5, so haploinsufficiency of CHD5 may contribute to the neurological and developmental abnormalities frequently encountered in patients afflicted with such syndromes (25).

Genes involved in chromatin remodeling play an important role in neoplasia. There are several cancer-specific rearrangements that have been shown recently to involve chromatin remodeling genes. Acute promyelocytic leukemia (APML), for example, results from translocations between the RARa gene on chromosome 17 and either the PML gene on chromosome 15 or the PLZF gene on chromosome 11 (26-28). These chimeric transcription factors interact with the SAP histone deacetylase complex. Retinoic acid, for example, can cause the release of the SAP complex from the RARa/PML complex, whereas it cannot cause dissociation in RARa/PLZF. The differences in these interactions may account for the differential responses of APML to retinoid therapy, depending on the type of translocation involved in the disease.

BRG1, a gene encoding a component of the Swi/Snf complex, has been implicated in growth control through its interaction with pRb, and Brg1 may be a negative regulator of proliferation. BRG1 has been shown recently to be mutated in multiple tumor cell lines, and reintroduction of this gene can reverse the transformed phenotype (29). In addition to pRb (30-32), chromatin remodeling proteins and complexes have been shown to interact with several other proteins involved in human neoplasia, such as the breast cancer protein BRCA1 (33), Myc networking proteins of the Mad family (Mad, Mxi1) (34-38), the DNA replication checkpoint gene ATR (39), and the HPV-E7 protein (40). These data reveal that alterations of gene expression mediated through chromatin remodeling may be critical for tumorigenesis in a variety of cancers.

CHD5 maps to a region that is frequently deleted in neuroblastomas and other neural crest tumors, so deletion of CHD5 may contribute to malignant transformation in neural tissue. Indeed, since CHD5 participates in a NuRD-type chromatin remodeling complex, the loss of expression of CHD5 gene and protein may prevent normal neuronal maturation of developing neuroblasts. Since this complex may inactivate proliferation-associated genes in neural tissues, loss of protein components of the larger complex could lock these cells in a proliferative mode and possibly prevent differentiation. Neuroblastomas are tumors of sympathetic neurons and commonly arise in the adrenal medulla and the sympathetic ganglionic chain. The CHD5 pattern of expression in developing neural tissues (brain and spinal cord) and adrenal glands, coupled with its activity, demonstrates that deletion of the CHD5 gene could contribute to the malignant transformation of neuroblasts. Elucidation of the normal function of the CHD5 gene and protein identified herein provides useful information regarding the role of CHD5 in neuroblastomas characterized by 1p deletions that result in loss or inactivation of CHD5.

Example II

Evaluation of CHD5 Mediated Chromatin Remodeling

Based on the nucleic acid sequence of CHD5, it likely functions as an ATP-dependent chromatin remodeling protein. CHD5 association with other proteins in a NuRD histone deacetylase (HDAC) complex, and CHD5 functions as an ATP-dependent chromatin remodeling protein within HDAC complexes, may be investigated utilizing techniques discussed below.

The following methods and materials are provided to facilitate practice of the present invention.

Immunoprecipitation and Western Blotting. Immunoprecipi-tations and western blotting with antibodies may be performed as previously described (41-44). Antibodies against HDAC1 and HDAC2 (as well as other HDACs), RbAp46 and RbAp48, Mi2, MTA1, MBD3, mSin3A and mSin3B, SAP18 and SAP3 are commercially available from Santa Cruz Biotechnology. Antibodies against many of these proteins are also available from Upstate Biotechnology or other venders. Antibodies are also available for other Swi/Snf-family proteins. The available antibodies are well suited for immunoprecipitation, Western and/or immunohistochemistry experiments. Detection of immunocomplexes may be conducted using an ECL chemiluminescence system (Amersham).

Methylation-specific PCR. Bisulfite-mediated chemical modification of DNA may be used to convert unmethylated cytosine to uracil, but leave methylated cytosine residues unaltered (CpGenome™, Intergen). Such modification may be followed by PCR with primers designed to distinguish methylated from unmethylated DNA (CpG Wiz Amplification kit, Intergen).

Histone Deacetylase and Nucleosome Remodeling Assays. The $^3$H-labeled acetylated core histones used for the deacetylase assay may be prepared from Jurkat or HeLa cells as described (45). A typical reaction may utilize 5 µl of beads loaded with 100-500 ng of the purified complex. The beads may be previously equilibrated with the deacetylase buffer (75 mM Tris-Cl pH 7.0, 100 mM NaCl, 2 mM b-mercaptoethanol, 0.1% EDTA). Ten micrograms of labeled core histones (2,000 cpm) may be added to each reaction for the assay using SDS-PAGE. ATP (1 mM), ATP-g-S (1 mM) and Trichostatin A (TSA) (300 nM) may be added as appropriate. The total volume of each reaction may be maintained at 20 µl by addition of deacetylase buffer. The reaction may proceed at 30° C. for 1 hr with mixing every 5 minutes, after which the reaction may be stopped by the addition of Laemmli buffer prior to fractionation on an 18% SDS-PAGE gel. The histones may be visualized on such gels by Coomassie blue staining. The gel may then be incubated with Amplify (Amersham), dried and autoradiographed with X-ray film.

For the liquid scintillation assay, 100 µg of core histones (20,000 cpm) may be added to each reaction. The released $^3$H-acetate may be extracted with ethyl acetate and quantified by liquid scintillation counting. The $^3$H-labeled acetylated oligonucleosomes may be prepared from HeLa cells using H1-depleted oligonucleosomes with an average length of 5 nucleosomes. Oligonucleosomes may be labeled in vitro with $^3$H-acetyl-CoA and NuA4, a HAT complex that specifically acetylates H4 and H2A (46). The mixture may then be fractionated on a Nick column (Pharmacia) to remove the unused $^3$H-acetyl-CoA. For each reaction, 180 ng of labeled nucleosomes (2,000 cpm) may be used. The reaction mixture may be analyzed by SDS-PAGE electrophoresis. The mononucleosome disruption assay may be performed as described (47-49).

Results

CHD5 polyclonal antibodies or monoclonal antiserum, as described hereinabove, may be used for immunoprecipitation and Western blotting studies to investigate the association of CHD5 with other proteins in the NuRD complex. CHD5 specific antibodies of the present invention may be used to immunoprecipitate CHD5 and associated proteins from lysates. (either before or after cross-linking to associated proteins). CHD5 immunoprecipitates may be analyzed by electrophoresis on a denaturing 18% SDS gel and visualized by staining to determine the number of proteins in the complex. Western blotting may also be used to identify any specific proteins that co-immunoprecipitate with CHD5. Antibodies of utility for such an analyses include, but are not limited to, the commercially available antibodies specific for RbAp46, RbAp48, Mta1/2, and MBD3 (Santa Cruz). Other antibodies may be similarly used to investigate the composition of CHD5 co-precipitating proteins. Antibodies against the histone deacetylases HDAC1 and HDAC2, for example, are also available commercially (Santa Cruz Biotechnology) and may be used to advantage in co-immunoprecipitation assays. Similar immunoprecipitation experiments may also be performed with anti-HDAC1 or anti-HDAC2 antibodies for the initial precipitation step followed by electrophoresis and Western blot analysis with the anti-CHD5 antibodies of the present invention. Results indicating that CHD5 co-immunoprecipitates with at least one protein known to be a component of a NuRD histone deacetylase complex would provide evidence that CHD5 is a bona fide component of the NuRD complex.

The role of CHD5 as a component of a NuRD complex may be investigated by performing chromatin remodeling assays. To test the ability of a NuRD complex comprising CHD5 to function in vitro, a large amount of such NuRD complexes may be isolated by affinity chromatography using antibodies as described above. Chromatin remodeling assays may be performed following a procedure similar to that used for CHD4 (16).

NuRD complexes comprising CHD5 may also be assessed for ATP-dependent chromatin remodeling activity using a mononucleosome disruption assay. Mononucleosome disruption assays may be performed with either naked DNA or nucleosome reconstituted DNA as a template. The pattern observed in mononucleosome disruption assays performed with and without the CHD5/NuRD complex may be compared to evaluate the effect of the complex on nucleosome structure. Such assays will be performed in the presence and absence of ATP to determine if ATP is required for CHD5/NuRD complex-mediated mononucleosome disruption. The degree of histone deacetylation may also be determined in the presence of CHD5/NuRD complexes. The effect of HDAC inhibitors, such as trapoxin (TPX) or trichostatin-A (TSA), may also be determined to investigate the role of histone deacetylation in the above processes.

Example III

Investigation of the Tumorigenic Potential of Exogenous CHD5 Expression and Identification of Downstream Genes Regulated by CHD5 Expression Levels The following methods and materials are provided to facilitate practice of the present invention.

Cell Lines. Forty-six well characterized neuroblastoma cell lines are available from the Children's Hospital of Philadelphia (CHOP) cell bank and are suitable for use in the methods described herein (10). The studies described herein focus primarily on five lines: SK-N-SH, SK-N-AS, NGP, CHP-134 and NBL-S (50). These lines have various combinations of 1p LOH, MYCN amplification and high MYCN expression and thus, facilitate testing of the effect of CHD5 expression in a variety of backgrounds in vitro and in vivo. Cells may be grown under standard culture conditions. For in vivo studies, cells may be mixed together and then divided into aliquots for each injection. Cells ($1\times10^7$) may be combined with 0.25 ml Matrigel prior to subcutaneous injection into the flank of each mouse.

Transfection. CHD5 expression may be analyzed for its effect on growth and tumorigenicity by subcloning the CHD5 gene into the pcDNA3.1 expression vector (Invitrogen) (pCHD5.WT) and transfecting by lipofection or electroporation into five representative neuroblastoma cell lines: SKNAS, CHP134, NGP, SKNSH, and NBL-S. Cell lines transfected with pCHD5.WT should express CHD5 constitutively. Cell lines may be transfected with vector having insert in the opposite (anti-sense) orientation as a control (pCHD5.AS) or with empty vector (pcDNA3.1). Transfected cells may be examined for effects on growth, differentiation, clonigenicity and tumorigenicity. For conditional expression studies, the CHD5 gene may be subcloned into an inducible expression system, such as, for example, the Tet-Regulated Expression System (Invitrogen), wherein it may be operably linked to the regulatory elements which confer inducible expression. Transfection may be performed as described herein and selection of stable, inducible transfectants performed by standard procedures.

Microarray Technique. For microarray experiments, RNA may be quantitated using the 2100 Bioanalyzer (Aligent Technologies). Probe may be prepared using 5-20 µg of total RNA or at least 1 µg of poly(A)+ RNA. First strand cDNA may be synthesized using Superscript II Reverse Transcriptase (Invitrogen) and a T7-(dT)$_{24}$ primer to incorporate the T7 priming site into the cDNA. Following RNA degradation with RNase H and second strand cDNA synthesis with T4 DNA polymerase, the double-stranded cDNA may be extracted with phenol:chloroform:isoamyl alcohol (25:24:1). About 1 µg of cDNA may be used as template in an in vitro transcription assay (IVTA) reaction (Enzo Biochem) which incorporates biotin into the resulting cRNA. The cRNA generated may be treated to produce fragments in a size range of 35-200 bases prior to use in hybridization. Fifteen µg of fragmented probe may be mixed with hybridization controls, herring sperm DNA, and acetylated BSA in hybridization buffer. The hybridization mixture may be heated at 99° C. for five minutes, incubated at 45° C. for five minutes and centrifuged at 13,000×g for 5 minutes. Test chips may be prehybridized with 80 µl of 1× hybridization buffer for 10 minutes at 45° C. at 60 RPM in a hybridization oven. Following removal of the prehybridization buffer, the chips may be filled with 80 μl of the hybridization mixture and incubated at 45° C. at 60 RPM for 16 hours.

Hybridization mixture may be removed and saved, and the chip filled with 100 μl of non-stringent wash buffer (6×SSPE; 0.01% Tween 20; 0.005% Antifoam). Further washing and staining of the chips may be conducted on the fluidics station with non-stringent washing buffer, stringent washing buffer (100 mM MES; 0.1 M [Na$^+$]; 0.01% Tween 20), and stain buffer (100 mM MES; 1 M [Na$^+$]; 0.05% Tween 20; 0.005% Antifoam) containing 10 μg/ml of streptavidin phycoerythrin (SAPE). Chips may be scanned and the data analyzed using the Affymetrix Microarray Suite software. If test chips produce satisfactory results, a U95A chip may be treated in the same manner, except that the hybridization volume may be 200 μl, the wash volume may be 250 μl and the signal may be amplified by an additional treatment with goat IgG (0.1 mg/ml), biotinylated antibody (3 μg/ml) and a second staining with SAPE. (Technical Manual, Affymetrix, Inc. 2000 (51). Photomultiplier output signals may be converted into proportional, spatially addressed pixel values using GeneChip software (Affymetrix) to create a digitized image. Probe Array Call Settings may be set, and average intensity calculated and assigned to a given X/Y coordinate and stored. Then the software may be used to apply a selected probe array algorithm to determine the expression levels for each gene. In a comparison analysis, one set of experimental data may be defined as the baseline and used for comparison to data from a second experiment. Probe Pair Masking may be performed to exclude probe pairs from analysis for technical or other reasons. Probe Set Mask files define specific probe sets for use during data scaling and normalization, which allows more accurate comparison of data from different experiments.

Animal Studies

Immunosuppressed Mice. Four- to 6-week-old female SCID/Beige mice may be obtained from Taconic Farms, Inc. and 4- to 6-week-old female athymic NCR (nu/nu) mice may be obtained from the NCI at Frederick, Md. Mice may be maintained at four per cage under humidity- and temperature-controlled conditions with a light/dark cycle set at 12-hour intervals. All animals may be fed water and autoclaved Purina mouse chow ad libitum. Mice may be weighed and their tumors measured with a Vernier caliper thrice per week following injection of neuroblastoma cells. Tumors may be measured in three dimensions ($d_1 \times d_2 \times d_3$) and tumor volume calculated by multiplying the product of 3 dimensions by n/6 (0.52). For neuroblastoma cell lines, ~$10^7$ cells/inoculate in RPM1-1640 may be injected subcutaneously into the flank, together with an equal volume of Matrigel (Becton Dickinson) (52, 53). The success rate of tumor development may be about 95%. Animals may be sacrificed in a $CO_2$ chamber.

Tumorigenicity Assays. Neuroblastoma xenografts may be comprised of either transfectants expressing CHD5 constitutively or transfectants expressing CHD5 inducibly, and appropriate controls thereto, as described hereinabove. Neuroblastoma xenografts may be grown and evaluated in immunosuppressed mice. About $10^7$ transfected neuroblastoma cells may be injected into the flank of 2-3 month old homozygous nu/nu mice, with 6-10 mice in each group injected with either the transfected or untransfected cell line. For mice injected with inducible expression constructs, 6-10 mice may be maintained in the presence of an agent (e.g., tetracycline or doxycycline) which regulates CHD5 expression, whereas 6-10 mice may be maintained in the absence of such an agent. Tumors may begin to develop within 10-14 days in ~95% of the mice injected. Mice may be assayed for: 1) the development of tumors at the injection site (or elsewhere); 2) the timing to develop tumors; and 3) the rate of tumor growth. Animals may be sacrificed once the tumor attains a size of ~5.0 cc, or sooner if the mice appear ill, uncomfortable, or stop eating.

Growth, Differentiation and Apoptosis.

Neuroblastomas which develop in vivo following injections of the transfected cell lines may be further evaluated ex vivo. Cell lines may be established from such neuroblastomas by growing the excised fragments of a tumor under appropriate tissue culture conditions. Once established, such cell lines may be analyzed to ascertain the role of CHD5 in a variety of cellular processes. CHD5 mediated effects on survival and growth, for example, may be studied by seeding multiple microwells with equivalent numbers of cells and determining the number of viable cells by MTT assay or by counting cells with Trypan Blue exclusion. For studies of differentiation, cultures may be examined daily for 7-14 days using photodocumentation. Cells with neurites at least three times the length of the cell body may be counted using photodocumentation. BrdU incorporation and staining of fixed cells may be used to detect cells in S-phase. Apoptosis may be detected using a system that measures TdT-incorporated dUTP nucleotide end labeling (TUNEL assay). Apoptosis may be confirmed by staining cells with Annexin-V and propidium iodide (Roche Molecular Biochemicals) according to the manufacturer's instructions. Apoptosis may also be demonstrated by gel electrophoresis of extracted DNA stained with ethidium bromide (EtBr) to detect the presence of a fragmented DNA ladder which is characteristic of inter-nucleosomal cleavage.

Clonigenicity Assays. Cell lines derived from transfected and untransfected neuroblastomas may be tested by dissociating cells in the exponential phase of growth and placing them on a layer of soft agar, overlaid with standard tissue culture medium plus G418. The number of colonies of transfected and untransfected cells may be counted three times a week for two weeks. All time points may be carried out in triplicate, and all experiments repeated at least once with each cell line. The triplicate results of each time point of each experiment may be averaged, standard errors calculated, and data points plotted on a bar graph. Differences between the transfected and untransfected cells of each line may be tested by Chi-square analysis.

Results

Assessment of the role of CHD5 in Tumorigenesis. The entire coding region of CHD5 (SEQ ID NO: 1) has been subcloned into the pcDNA3.1 plasmid in which its expression is regulated by a CMV promoter (pCHD5.WT). The pCHD5.WT expression construct has been resequenced to confirm the sequence of the insert and the insertion site. The CHD5 expression construct has been transfected into a plurality of neuroblastoma cell lines using the Lipofection technique. Specifically, SK-N-AS and CHP-134, which have gross 1p deletions, and SK-N-SH and NGP, which lack gross 1p deletions have been transfected and single-cell clones have been identified in selective media containing G418. To provide controls for these experiments, constructs having the CHD5 cDNA in the opposite or anti-sense orientation (pCHD5.AS), as well as a vector without insert (pcDNA3.1) may be transfected.

The tumorigenic potential of CHD5-transfected and control transfected neuroblastoma cell lines may be assessed in vivo. Tumorigenicity may be evaluated by injecting an equivalent number of transfected cells into the flanks of immunosuppressed mice [nude (nu/nu) or SCID/Beige] and monitoring the animals for tumor growth. Tumors may be measured thrice weekly until the tumors reach a size of ~5 cc, after which the animals will be sacrificed. The CHD5 gene may also be introduced in a similar system under the control of a Tet-inducible promoter. In this system, large numbers of cells may be generated in the absence of transgene (e.g., CHD5) expression prior to injection into animals. Upon formation of a palpable tumor, animals will receive feed containing the inducing agent (e.g., tetracycline) to observe the effects of CHD5 expression on tumor growth. Any tumors that develop from CHD5 transfected cells will be examined for possible loss or mutation of the CHD5 gene, or absence of expression of the gene at the mRNA and protein levels to identify revertants.

Utilizing the above in vivo system, the consequences of CHD5 transfection on cell survival and gross morphology may also be determined. Neuroblastoma tumors which develop in animals following transfer of transfected cells may be excised and further analyzed in vitro. Cell lines may be developed from the excised tumors and evaluated for differences in morphology and survival in the presence or absence of CHD5 expression. Cell viability, for example, may be determined by counting the number of living cells using the MTT assay or Trypan Blue exclusion at several time points over a 2-4 week period. In addition to determining the rate of growth, the proliferative index is measurable by BrdU and/or PCNA staining. The rate of programmed cell death may be determined using TUNEL and Annexin V staining. The morphology of neuroblastoma cell lines developed from explanted tumors may also be examined in the presence and absence of CHD5 expression by phase microscopy with photodocumentation.

Identification of Genes Whose Expression is Modulated by CHD5 Expression Levels. Expression of the CHD5 gene may also be examined in the context of a neuroblastoma cell line having undetectable levels of CHD5 as determined by RT-PCR (See Example I). The CHD5 gene may be placed under the control of a conditional promoter (e.g., Tet-on) which may be regulated readily by altering the composition of the cellular growth media. In one embodiment, the SK-N-AS neuroblastoma cell line, which has a small 1p deletion that includes the CHD5 gene and no MYCN amplification, may be transfected with a vector comprising the CHD5 gene under the control of a conditional promoter. In another embodiment, the CHP-134 neuroblastoma cell line, which has a larger 1p deletion and MYCN amplification, may also be transfected with a vector comprising the CHD5 gene under the control of a conditional promoter. Transfection of both of these representative neuroblastoma cell lines provides a comparative system in which to assess the effects of CHD5 expression in the absence and presence of high MYCN expression.

Expression of CHD5 may be induced using such Tet-inducible neuroblastoma systems, from which RNA samples may be isolated at selected times following induction (e.g., 0, 1 hr, 4 hr, 8 hr). RNA samples derived from temporally distinct CHD5 transfectants (uninduced and induced to express CHD5) provide reagents of utility in the identification of genes that are differentially expressed in response to CHD5 levels. In a preferred embodiment, Affymetrix GeneChip U95A will be used for the identification of genes that are differentially expressed in response to CHD5 levels. Affymetrix GeneChip U95A arrays contain oligonucleotides representing 12,000 well-characterized genes, rendering it likely that genes which are differentially regulated by CHD5 expression may be identified.

Example IV

Screening Neuroblastoma Cell Lines and Patient Samples for alterations in the CHD5 Gene The following methods and materials are provided to facilitate practice of the present invention.

Molecular and Protein Studies

DNA preparation and Southern analysis may be performed as described herein and utilizing standard techniques.

RNA preparation and Northern analysis may be performed as described herein utilizing standard techniques.

PCR and RT-PCR will be performed as described hereinabove. See Example I.

DNA Sequencing. Bidirectional sequencing of DNAs from plasmids, cosmids, PACs and PCR products may be performed using an automated Applied Biosystems, Inc. (ABI) Model 3700 capillary sequencer. Analysis of DNA and protein sequence will be performed with software packages GenoMax or MacVector.

Southern blot analysis of DNA extracted from neuroblastoma cell lines, representative primary neuroblastomas, and tumor samples derived from patients may be used to determine if the CHD5 gene is deleted or rearranged in such cells. Significantly, neuroblastoma cell lines and representative primary neuroblastomas, either with or without 1p LOH, will be assessed. The prevalence of mutations in sporadic and familial neuroblastomas, and in tumors with and without 1p LOH and/or MYCN amplification may also be examined. Northern and RT-PCR analysis may also be of utility in the analysis of lines and tumors that lack detectable rearrangements of CHD5 but express the gene inappropriately (e.g., altered molecular weight and/or amount). To determine if tumors that lack CHD5 expression, but do not exhibit gross CHD5 rearrangements, possess other mutations or are differentially methylated, the CHD5 promoter regions may also be sequenced. In cases with apparent rearrangements of the DNA or mRNA, sequencing may be performed to determine the nature of these rearrangements. A variety of assays may be used for the analysis of genetic mutations, including: allele-specific oligonucleotide assay, denaturing high-performance liquid chromatography, protein truncation assay, denaturing gradient gel electrophoresis, restriction digestion of PCR products, or direct sequencing with fluorescently labeled primers. One of skill in the art would appreciate that the choice(s) of assay for a particular analysis depends upon the nature of the rearrangement or mutation involved. The identification of mutational hotspots within CHD5 may be exploited to develop rapid assays for detection of common mutations.

Example V

Screening Neuroblastoma Cell Lines and Patient Samples for Alterations in Other Genes Localized to 1p36.3

Neuroblastoma, a tumor of the postganglionic sympathetic nervous system, is the most common and deadly solid tumor of childhood. Interestingly, certain infants, even with metastatic disease, experience complete regression of their disease without therapy, whereas other patients have maturation of their tumor into benign ganglioneuromas. Unfortunately, the majority of tumors are metastatic at diagnosis, and many progress relentlessly despite the most intensive multimodality therapy. Indeed, despite dramatic improvements in the cure rate for many other common pediatric neoplasms, the improvement in the overall survival rate for patients with neuroblastoma has lagged behind. However, recent advances in neuroblastoma research have provided considerable insight into different patterns of genetic change underlying these seemingly disparate behaviors.

Deletion or loss of heterozygosity (LOH) for the short arm of chromosome 1 (1p) is the most characteristic genetic change observed in neuroblastomas and certain other cancers. The present inventors have mapped the region of consistent loss to ~800 kb on 1p36.3, which comprises certain other genes, including CHD5 (as described hereinabove). This region maps between the proximal marker D1S253 and the distal marker D1S2660, thus comprising the smallest region of overlap (SRO) or consistent loss identified to date. Thus, methods for screening for the loss of other genes including but not limited to KCNAB2, RPL22, ICMT, and HBACH are also encompassed by the present invention.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

REFERENCES

1. Struhl, K. (1998) *Genes & Development* 12, 599-606.
2. Sudarsanam, P. & Winston, F. (2000) *Trends in Genetics* 16, 345-51.
3. Woodage, T., Basrai, M. A., Baxevanis, A. D., Hieter, P. & Collins, F. S. (1997) *Proceedings of the National Academy of Sciences, U.S.A.* 94, 11472-7.
4. Brodeur, G. M., Maris, J. M., Yamashiro, D. J., Hogarty, M. D. & White, P. S. (1997) *Journal of Pediatric Hematology-Oncology* 19, 93-101.
5. Hogarty, M. D., Liu, X., Guo, C., Thompson, P. M., Weiss, M. J., White, P. S., Sulman, E. P., Brodeur, G. M. & Maris, J. M. (2000) *Medical and Pediatric Oncology* 35, 512-515.
6. Maris, J. M., Guo, C., Blake, D., White, P. S., Hogarty, M. D., Thompson, P. M., Rajalingam, V., Gerbing, R., Stram, D. O., Matthay, K. K., Seeger, R. C. & Brodeur, G. M. (2001) *Medical and Pediatric Oncology* 36, 32-36.
7. White, P. S., Maris, J. M., Sulman, E. P., Jensen, S. J., Kyemba, S. M., Beltinger, C. P., Allen, C., Kramer, D. L., Biegel, J. A. & Brodeur, G. M. (1997) *European Journal of Cancer* 33, 1957-61.
8. Tatusova, T. A. & Madden, T. L. (1999) *FEMS Microbiology Letters* 174, 247-50.
9. Reese, M. G., Hartzell, G., Harris, N. L., Ohler, U., Abril, J. F. & Lewis, S. E. (2000) *Genome Research* 10, 483-501.
10. Thompson, P. M., Maris, J. M., Hogarty, M. D., Seeger, R. C., Reynolds, C. P., Brodeur, G. M. & White, P. S. (2001) *Cancer Research* 61, 679-686.
11. Maris, J. M., Jensen, S. J., Sulman, E. P., Beltinger, C. P., Gates, K., Allen, C., Biegel, J. A., Brodeur, G. M. & White, P. S. (1996) *Genomics* 35, 289-98.
12. White, P. S., Thompson, P. M., Gotoh, T., Maris, J. M., Hogarty, M. D. & Brodeur, G. M. (2001) (submitted).
13. Bentley, D. R., Deloukas, P., Dunham, A., French, L., Gregory, S. G., Humphray, S. J., Mungall, A. J., Ross, M. T., Carter, N. P., Dunham, I., Scott, C. E., Ashcroft, K. J., Atkinson, A. L., Aubin, K., Beare, D. M., Bethel, G., Brady, N., Brook, J. C., Burford, D. C., Burrill, W. D., Burrows, C., Butler, A. P., Carder, C., Catanese, J. J., Clee, C. M., Clegg, S. M., Cobley, V., Coffey, A. J., Cole, C. G., Collins, J. E., Conquer, J. S., Cooper, R. A., Culley, K. M., Dawson, E., Dearden, F. L., Durbin, R. M., de Jong, P. J., Dhami, P. D., Earthrowl, M. E., Edwards, C. A., Evans, R. S., Gillson, C. J., Ghori, J., Green, L., Gwilliam, R., Halls, K. S., Hammond, S., Harper, G. L., Heathcott, R. W., Holden, J. L., Holloway, E., Hopkins, B. L., Howard, P. J., Howell, G. R., Huckle, E. J., Hughes, J., Hunt, P. J., Hunt, S. E., Izmajlowicz, M., Jones, C. A., Joseph, S. S., Laird, G., Langford, C. F., Lehvaslaiho, M. H., Leversha, M. A., McCann, O. T., McDonald, L. M., McDowall, J., Maslen, G. L., Mistry, D., Moschonas, N. K., Neocleous, V., Pearson, D. M., Phillips, K. J., Porter, K. M., Prathalingam, S. R., Ramsey, Y. H., Ranby, S. A., Rice, C. M., Rogers, J., Rogers, L. J., Sarafidou, T., Scott, D. J., Sharp, G. J., Shaw-Smith, C. J., Smink, L. J., Soderlund, C., Sotheran, E. C., Steingruber, H. E., Sulston, J. E., Taylor, A., Taylor, R. G., Thorpe, A. A., Tinsley, E., Warry, G. L., Whittaker, A., Whittaker, P., Williams, S. H., Wilmer, T. E., Wooster, R., et al. (2001) *Nature* 409, 942-3.
14. Kozak, M. (2000) *Genomics* 70, 396-406.
15. Tong, J. K., Hassig, C. A., Schnitzler, G. R., Kingston, R. E. & Schreiber, S. L. (1998) *Nature* 395, 917-21.
16. Xue, Y., Wong, J., Moreno, G. T., Young, M. K., Cote, J. & Wang, W. (1998) *Molecular Cell* 2, 851-61.
17. Delmas, V., Stokes, D. G. & Perry, R. P. (1993) *Proceedings of the National Academy of Sciences, U.S.A.* 90, 2414-8.
18. Ge, Q., Nilasena, D. S., O'Brien, C. A., Frank, M. B. & Targoff, I. N. (1995) *Journal of Clinical Investigation* 96, 1730-7.
19. Seelig, H. P., Moosbrugger, I., Ehrfeld, H., Fink, T., Renz, M. & Genth, E. (1995) *Arthritis and Rheumatology* 38, 1389-99.
20. Zhang, Y., LeRoy, G., Seelig, H. P., Lane, W. S. & Reinberg, D. (1998) *Cell* 95, 279-89.
21. Ahringer, J. (2000) *Trends in Genetics* 16, 351-6.
22. Kehle, J., Beuchle, D., Treuheit, S., Christen, B., Kennison, J. A., Bienz, M. & Muller, J. (1998) *Science* 282, 1897-900.
23. Muller, J. (1995) *EMBO Journal* 14, 1209-20.
24. Slavotinek, A., Shaffer, L. G. & Shapira, S. K. (1999) *Journal of Medical Genetics* 36, 657-63.
25. Wu, Y. Q., Heilstedt, H. A., Bedell, J. A., May, K. M., Starkey, D. E., McPherson, J. D., Shapira, S. K. & Shaffer, L. G. (1999) *Human Molecular Genetics* 8, 313-21.
26. Grignani, F., De Matteis, S., Nervi, C., Tomassoni, L., Gelmetti, V., Cioce, M., Fanelli, M., Ruthardt, M., Ferrara, F. F., Zamir, I., Seiser, C., Lazar, M. A., Minucci, S. & Pelicci, P. G. (1998) *Nature* 391, 815-8.
27. Kitamura, K., Hoshi, S., Koike, M., Kiyoi, H., Saito, H. & Naoe, T. (2000) *British Journal of Haematology* 108, 696-702.
28. Lin, R. J., Nagy, L., Inoue, S., Shao, W., Miller, W. H., Jr. & Evans, R. M. (1998) *Nature* 391, 811-4.
29. Wong, A. K., Shanahan, F., Chen, Y., Lian, L., Ha, P., Hendricks, K., Ghaffari, S., Iliev, D., Penn, B., Woodland, A. M., Smith, R., Salada, G., Carillo, A., Laity, K., Gupte, J., Swedlund, B., Tavtigian, S. V., Teng, D. H. & Lees, E. (2000) *Cancer Research* 60, 6171-7.
30. Brehm, A., Miska, E. A., McCance, D. J., Reid, J. L., Bannister, A. J. & Kouzarides, T. (1998) *Nature* 391, 597-601.
31. Luo, R. X., Postigo, A. A. & Dean, D. C. (1998) *Cell* 92, 463-73.

32. Magnaghi-Jaulin, L., Groisman, R., Naguibneva, I., Robin, P., Lorain, S., Le Villain, J. P., Troalen, F., Trouche, D. & Harel-Bellan, A. (1998) *Nature* 391, 601-5.

33. Yarden, R. I. & Brody, L. C. (1999) *Proceedings of the National Academy of Sciences, U.S.A.* 96, 4983-8.

34. Ayer, D. E., Lawrence, Q. A. & Eisenman, R. N. (1995) *Cell* 80, 767-76.

35. Schreiber-Agus, N., Chin, L., Chen, K., Torres, R., Rao, G., Guida, P., Skoultchi, A. I. & DePinho, R. A. (1995) *Cell* 80, 777-86.

36. Harper, S. E., Qiu, Y. & Sharp, P. A. (1996) *Proceedings of the National Academy of Sciences, U.S.A.* 93, 8536-40.

37. Kasten, M. M., Ayer, D. E. & Stillman, D. J. (1996) *Molecular and Cellular Biology* 16, 4215-21.

38. Schreiber-Agus, N. & DePinho, R. A. (1998) *Bioessays* 20, 808-18.

39. Schmidt, D. R. & Schreiber, S. L. (1999) *Biochemistry* 38, 14711-7.

40. Brehm, A., Nielsen, S. J., Miska, E. A., McCance, D. J., Reid, J. L., Bannister, A. J. & Kouzarides, T. (1999) *EMBO Journal* 18, 2449-58.

41. Cohn, S. L., Salwen, H., Quasney, M. W., Ikegaki, N., Cowan, J. M., Herst, C. V., Kennett, R. H., Rosen, S. T., DiGiuseppe, J. A., and Brodeur, G. M. (1990) *Oncogene* 5, 1821-1827.

42. Eggert, A., Ho, R., Ikegaki, N., Liu, X., and Brodeur, G. M. (2000) *Med Pediatr Oncol.* 35, 623-627.

43. Eggert, A., Ikegaki, N., Liu, X.-G., Chou, T. T., Lee, V. M., Trojanowski, J. Q., and Brodeur, G. M. (2000) *Oncogene* 19, 2043-2051.

44. Eggert, A., Sieverts, H., Ikegaki, N., and Brodeur, G. M. (2000) *Med Pediatr Oncol.* 35, 573-576.

45. Rundlett, S. E., Carmen, A. A., Kobayashi, R., Bavykin, S., Turner, B. M., and Grunstein, M. (1996) *Proc Natl Acad Sci USA.* 93, 14503-8.

46. Grant, P. A., Duggan, L., Cote, J., Roberts, S. M., Brownell, J. E., Candau, R., Ohba, R., Owen-Hughes, T., Allis, C. D., Winston, F., Berger, S. L., and Workman, J. L. (1997) *Genes Dev.* 11, 1640-50.

47. Owen-Hughes, T. and Workman, J. L. (1996) *EMBO Journal.* 15, 4702-12.

48. Owen-Hughes, T., Utley, R. T., Steger, D. J., West, J. M., John, S., Cote, J., Havas, K. M., and Workman, J. L. (1999) *Methods Mol. Biol.* 119: 319-31.

49. Wang, W., Chi, T., Xue, Y., Zhou, S., Kuo, A., and Crabtree, G. R. (1998) *Proc Natl Acad Sci USA.* 95: 492-8.

50. Reynolds, C. P., Tomayko, M. M., Donner, L., Helson, L., Seeger, R. C., Triche, T. J., and Brodeur, G. M. (1988) *Prog Clin Biol Res.* 271, 291-306.

51. Lipshutz, R. J., Fodor, S. P. A., Gingeras, T. R., and Lockhart, D. J. (1999) *Nat Genet.* 21, 20-24.

52. White, P. S., Thompson, P. M., Seifried, B. A., Sulman, E. P., Jensen, S. J., Guo, C., Maris, J. M., Hogarty, M. D., Allen, C., Biegel, J. A., Matise, T. C., Gregory, S. G., Reynolds, C. P., and Brodeur, G. M. (2001) *Med Pediatr Oncol.* 36, 37-41.

53. Caron, H., Peter, M., van Sluis, P., Speleman, F., de Kraker, J., Laureys, G., Michon, J., Brugieres, L., Voute, P. A., Westerveld, A., Slater, R., Delattre, O., and Versteeg, R. (1995) *Hum Mol Genet.* 4, 535-539.

---

What is claimed is:

1. An isolated nucleic acid molecule encoding a human chromodomain helicase DNA-binding 5 (CHD5) protein, said CHD5 protein being about 1954 amino acids in length and comprising an amino terminus comprising two PHD class zinc finger domains and two chromodomains, a central region comprising a DEAH-box-type helicase domain and a SNF2 domain, and a plurality of nuclear localization signals, and wherein said CHD5 comprises the amino acid sequence of SEQ ID NO: 2 wherein said nucleic acid molecule is a cDNA.

2. The nucleic acid molecule of claim 1, which is a cDNA molecule comprising a sequence approximately 9,646 base pairs in length.

3. The nucleic acid molecule of claim 2, wherein said cDNA molecule comprises the nucleic acid sequence of SEQ ID NO: 1.

4. An isolated nucleic acid molecule encoding a human chromodomain helicase DNA-binding 5 (CHD5) protein, said CHD5 protein being about 1954 amino acids in length and comprising an amino terminus comprising two PHD class zinc finger domains and two chromodomains, a central region comprising a DEAH-box-type helicase domain and a SNF2 domain, and a plurality of nuclear localization signals, and wherein said CHD5 comprises the amino acid sequence of SEQ ID NO: 2, wherein said nucleic acid molecule is RNA.

5. An isolated polynucleotide which comprises a sequence fully complementary to the complete sequence of SEQ ID NO: 1.

6. An isolated vector comprising the nucleic acid molecule of claim 1.

7. The isolated vector of claim 6 selected from the group consisting of a plasmid, an adenovirus vector, an adenovirus associated vector, and a retroviral vector.

8. An isolated host cell comprising the vector of claim 6.

9. The isolated host cell of claim 8, which is selected from the group consisting of bacterial, fungal, mammalian, insect and plant cells.

10. The isolated host cell of claim 8, wherein said nucleic acid molecule is provided in a vector and is operably linked to mammalian regulatory elements.

11. A pair of CHD5-specific PCR primers suitable for amplifying the nucleic acid of claim 1, wherein the pair of primers are selected from the group provided in Table I, and wherein one primer of said pair of primers consists of SEQ ID NO: 8.

12. A kit comprising the pair of CHD5-specific PCR primers of claim 11.

13. A kit for diagnosing a tumor in a patient, said kit comprising:
   a) a container for storing a biological sample obtained from said patient;
   b) a composition comprising one or more nucleic acid molecules which is fully complementary to the complete sequence of the nucleic acid molecule of claim 1 in an amount effective to permit detection of a CHD5 encoding nucleic acid molecule, if present, in said sample; and
   c) instructional material setting forth a protocol suitable for use in detecting and quantifying said CHD5 encoding nucleic acid molecule.

14. A kit for diagnosing a tumor in a patient, said kit comprising:
   a) a container for storing a biological sample obtained from said patient;
   b) a composition comprising one or more nucleic acid molecules which is fully complementary to the complete sequence of the nucleic acid molecule of claim 4 in an amount effective to permit detection of a CHD5 encoding nucleic acid molecule, if present, in said sample; and
   c) instructional material setting forth a protocol suitable for use in detecting and quantifying said CHD5 encoding nucleic acid molecule.

\* \* \* \* \*